(12) United States Patent
Cumbo et al.

(10) Patent No.: US 12,312,579 B2
(45) Date of Patent: *May 27, 2025

(54) **METHOD FOR CULTURING *H. pylori* FOR FUTURE TESTING**

(71) Applicant: BioSherpa, LLC, Lewiston, NY (US)

(72) Inventors: Thomas A. Cumbo, Lewiston, NY (US); Christopher L Hutson, Houston, TX (US); Destin J. Radder, Lewiston, NY (US)

(73) Assignee: BioSherpa, LLC, Lewiston, NY (US)

( * ) Notice: Subject to any disclaimer, the term of this patent is extended or adjusted under 35 U.S.C. 154(b) by 1010 days.

This patent is subject to a terminal disclaimer.

(21) Appl. No.: 17/354,218

(22) Filed: Jun. 22, 2021

(65) Prior Publication Data
US 2021/0309959 A1   Oct. 7, 2021

Related U.S. Application Data

(63) Continuation of application No. 16/925,170, filed on Jul. 9, 2020, now Pat. No. 11,072,775.

(60) Provisional application No. 62/873,421, filed on Jul. 12, 2019.

(51) Int. Cl.
| | | |
|---|---|---|
| *C12N 1/04* | (2006.01) | |
| *C12N 1/20* | (2006.01) | |
| *C12N 1/32* | (2006.01) | |

(52) U.S. Cl.
CPC ............... *C12N 1/04* (2013.01); *C12N 1/20* (2013.01); *C12N 1/32* (2013.01)

(58) Field of Classification Search
CPC ............... C12N 1/04; C12N 1/32; C12N 1/20
See application file for complete search history.

(56) References Cited

U.S. PATENT DOCUMENTS

| | | | |
|---|---|---|---|
| 11,072,775 B2 * | 7/2021 | Cumbo | ............ C12N 1/20 |
| 2007/0122872 A1 * | 5/2007 | Cumbo | ............ C12Q 1/045 |
| | | | 435/287.1 |

* cited by examiner

*Primary Examiner* — Louise W Humphrey
*Assistant Examiner* — Anjali Ajit Hirani
(74) *Attorney, Agent, or Firm* — KNOBBE, MARTENS, OLSON & BEAR, LLP

(57) ABSTRACT

The present application provides systems and methods for storing biological samples, including a transport medium configured to protect bacterial viability and optimize sample quality, for enhanced diagnostic accuracy. The systems and methods can include a transport media, a collection tube including a screen and sampling brush, and a transport case. The systems and methods allow samples to be frozen and thawed while preserving cellular wall integrity during transport or storage, and furthermore can preserve the survival of the bacterial sample, enabling more accurate detection of an infectious agent.

20 Claims, 38 Drawing Sheets

● - Infectious bacteria (target)
● - Benign colonizing bacteria

● - Infectious bacteria (target)
● - Benign colonizing bacteria

METHOD FOR CULTURING *H. pylori* FOR FUTURE TESTING

PRIORITY CLAIM

This application is a continuation of U.S. application Ser. No. 16/925,170, filed on Jul. 9, 2020, which claims the benefit under 35 U.S.C. 119 (e) to U.S. Prov. App. No. 62/873,421 filed on Jul. 12, 2019, the entire contents of each of which is hereby incorporated by reference in its entirety.

BACKGROUND

Field of the Invention

The invention relates, in some aspects, to improved biological transport systems and methods.

Description of the Related Art

Many infectious organisms thrive in the body primarily as biofilms. Biofilms are colonies of bacteria encased in a secreted gel-like substance which confer protection from, for example, immunological agents and antibiotics. Biofilms negatively impact the bacterial culturing process in several ways. As one example, biofilm sequestration in a sample represents a non-random distribution of bacteria that when sampled for culture may yield a spurious negative result. As another example, current laboratory practice is geared to culturing the planktonic or free-floating stage of bacteria not organisms aggregated in biofilms. Together, these issues decrease the accuracy of the culture process in the laboratory, and can increase the time to proper diagnosis (slower growth).

When a sample is taken from a patient and not immediately cultured, infectious organisms may quickly die before culture while beneficial bacteria survive negatively impacting diagnostic cultures in two ways. First, the death of pathogenic bacteria results in false negative results leading to a suboptimal (or even misguided) treatment plan. Second, the disproportionate quantity of colonizing bacteria over pathogenic ones leads to colonizer overgrowth in culture which can obscure detection of disease-causing organisms. These two effects are exacerbated by centralization of laboratory services which increases the time from sample collection to diagnostic culture. That increase in time further exposes pathogenic bacteria to the elements and increases the likelihood that these bacteria will die off prior to culture. The result is an indeterminate culture preventing proper treatment.

The inability to correctly and accurately identify an infectious organism can have several adverse consequences, including but not limited to: the inability to make an exact diagnosis; the use of multiple broad spectrum antibiotics for longer periods of time; longer hospital stays at greater cost; lower probability of a complete and timely recovery; a greater probability of complications such as antibiotic resistance, secondary infections (e.g., (. *difficile*); the spread of nosocomial infections throughout the medical facility; and lower insurance reimbursements to the doctors/hospital.

Improved clinical transport systems that allow for prolonged specimen survival and enhanced pathogen retrieval are needed.

SUMMARY

In some embodiments, disclosed herein is a biological transport media, including any number of features disclosed herein.

In some embodiments, disclosed herein is a sample transport tube system, including any number of features disclosed herein.

In some embodiments, disclosed herein is a sample transport tube system which incorporates a sampling brush.

In some embodiments, disclosed herein the method can also include agitating the sample prior to sampling for culture.

In some embodiments, disclosed herein is an infectious organism transport media, including any number of: about, or at least about 50%, 65%, 80%, or more of glycerol, and at least about 5%, 10%, or more of a mucolytic agent. The media does not include, or does not substantially include any additional infectious organism growth media.

In some embodiments, the mucolytic agent is Sputolysin® (Dithiothreitol).

In some embodiments, the transport media consists essentially of, or consists of glycerol and the mucolytic agent.

In some embodiments, disclosed herein is a method of transporting a biological sample, comprising collecting the biological sample from a subject; and contacting the biological sample with a transport media. The transport media can include at least about 50% glycerol; and at least about 5% of a mucolytic agent. In some embodiments, the media does not include any additional growth media. In some embodiments, the method improves yield and/or diagnosis of the biological sample. In some embodiments, the remainder of the transport media that is not glycerol or additional growth media is a sterile fluid such as, for example, free water or saline.

In some embodiments, contacting the sample with a transport media comprises placing the biological sample within a transport tube.

In some embodiments, the transport tube can include one, two, or more screens, which can have a conical geometry or a cylindrical geometry directly adjacent a conical geometry.

In some embodiments, the method can also include transporting the biological sample to a sample diagnostic center.

In some embodiments, the method can also include cooling the biological sample.

In some embodiments, the method can also include shaking the biological sample prior to cooling.

In some embodiments, disclosed herein the method can also include incubating the sample at 37 degrees Celsius for up to 24 hours.

In some embodiments, the method can also include moving the conical screen to a closed distal end of the transport tube.

In some embodiments, cooling the biological sample includes freezing the biological sample.

Also disclosed herein is an infectious organism transport system, that can include a transport media including, for example, any number of features as disclosed herein, and a transport tube including, for example, any number of features as disclosed herein.

In some embodiments, the transport system can also include a storage case including a plurality of wells configured to fit a plurality of transport tubes.

In some embodiments, the transport system can also include a cooling container. The cooling container can include a cavity configured to house the storage case therein.

In some embodiments, the transport system can also include a case, e.g., a Pelican case configured to house the cooling container therein.

In some embodiments, the transport tube includes a generally conical, or generally flat distal end.

In some embodiments, the transport tube can also include an open end that has a diameter greater than, or equal to that of a diameter of a more distal tubular portion of the transport tube.

Also disclosed herein is a modular biological sample container, including one or more of: a top end comprising a first lumen configured to be reversibly closed with a first cap; a bottom end comprising a second lumen configured to be reversibly closed with a second cap; a funnel portion proximate the top end; a cylindrical portion proximate the funnel portion; and a transition zone between the funnel portion and the cylindrical portion, the transition zone comprising reversible connectors configured such that the funnel portion can be reversibly attached and/or detached from the cylindrical portion.

In some embodiments, the sample container also includes a screen within the cylindrical portion.

In some embodiments, the first lumen includes a diameter greater than a diameter of the second lumen.

In some embodiments, the reversible connectors comprise threaded surfaces.

In some embodiments, the threaded surfaces include an inner sidewall of the funnel portion and an outer sidewall of the cylindrical portion.

In some embodiments, the sample container includes threaded surfaces proximate the top end and the bottom end.

Also disclosed herein is a modular biological sample kit, including a sample container including any number of features as disclosed herein, and a cap configured to reversibly close the transition zone following detachment of the funnel portion from the cylindrical portion.

In some embodiments, a system, device, transport media, or method can comprise, consist essentially of, or consist of any number of features of this disclosure.

In some embodiments, an infectious organism transport media is provided. The infectious organism transport media can comprise at least about 50% glycerol. The infectious organism transport media can comprise at least about 5% of a mucolytic agent. In some embodiments, the infectious organism transport media does not include any additional infectious organism growth agent.

In some embodiments, the transport media can comprise at least about 65% glycerol. In some embodiments, the transport media can comprise at least about 80% glycerol. In some embodiments, the transport media can comprise at least about 10% of a mucolytic agent. In some embodiments, the mucolytic agent comprises Sputolysin® (Dithiothreitol). In some embodiments, the transport media can consist essentially of glycerol and mucolytic agent. In some embodiments, the transport media consists of glycerol and mucolytic agent.

In some embodiments, a method of transporting a biological sample is provided. The method can comprise collecting the biological sample from a subject. The method can comprise contacting the biological sample with a transport media. In some embodiments, the transport media comprises at least about 50% glycerol and at least about 5% of a mucolytic agent. In some embodiments, the transport media does not include any additional growth media. In some embodiments, the method improved yield and/or diagnosis of the biological sample.

In some embodiments, contacting the sample with a transport media comprises placing the biological sample within a transport tube. In some embodiments, the transport tube comprises a screen. In some embodiments, the screen comprises a conical screen. In some embodiments, the method can comprise moving the conical screen to a closed distal end of the transport tube. In some embodiments, the transport tube comprises an integrated sampling brush. In some embodiments, the method can comprise transporting the biological sample to a sample diagnostic center. In some embodiments, the method can comprise cooling the biological sample. In some embodiments, the method can comprise shaking the biological sample prior to cooling. In some embodiments, cooling the biological sample comprises freezing the biological sample. In some embodiments, the method can comprise agitating the sample to homogenize the specimen prior to culture. In some embodiments, the method can comprise incubating the sample at 37 degrees Celsius for up to 24 hours to increase the density of pathogenic bacteria prior to culture.

In some embodiments, an infectious organism transport system is provided. The transport system can comprise a transport media as described herein. The transport system can comprise a transport tube.

In some embodiments, the transport tube comprises a screen. In some embodiments, the screen comprises a conical screen. In some embodiments, the screen is axially movable. In some embodiments, the transport system can comprise a storage case comprising a plurality of wells configured to fit a plurality of transport tubes. In some embodiments, the transport system can comprise a cooling container, the cooling container comprising a cavity configured to house the storage case therein. In some embodiments, the transport system can comprise a Pelican case configured to house the cooling container therein. In some embodiments, the transport tube comprises a generally conical distal end. In some embodiments, the transport tube comprises a generally flat distal end. In some embodiments, the transport tube comprises an open end that comprises a diameter greater than that of a diameter of a more distal tubular portion of the transport tube. In some embodiments, the transport tube comprises an open end that comprises a diameter equal to that of a diameter of a more distal tubular portion of the transport tube.

In some embodiments, modular biological sample container is provided. The sample container can comprise an upper section comprising a first lumen configured to be reversibly closed with a first cap. The sample container can comprise a lower section comprising a second lumen configured to be reversibly closed with a second cap. The sample container can comprise a funnel portion proximate a top end of the upper section. The sample container can comprise a cylindrical portion proximate the funnel portion. The sample container can comprise a transition zone between the funnel portion and the cylindrical portion. The sample container can comprise reversible connectors configured such that the upper section can be reversibly attached and/or detached from the lower section.

In some embodiments, the sample container can comprise a screen within the lower section. In some embodiments, the first lumen comprises a diameter greater than a diameter of the second lumen. In some embodiments, the reversible connectors comprise threaded surfaces. In some embodiments, the threaded surfaces comprise an inner sidewall of the upper section and an outer sidewall of the lower section. In some embodiments, the sample container can comprise threaded surfaces proximate a top end of the upper section and a bottom end of the lower section. In some embodiments, the second cap is removably coupled to the bottom end of the lower section when the upper section is coupled to the lower section.

In some embodiments, a modular biological sample kit is provided. The kit can comprise the sample container described herein. The kit can comprise a third cap configured to reversibly close the transition zone following detachment of the funnel portion from the cylindrical portion.

In some embodiments, a screen for a modular biological transport container is provided. The screen can comprise a first open end comprising a first diameter. The screen can comprise a second open end comprising a second diameter. The screen can comprise a conical section comprising a sidewall defining a flow path between the first open end and the second open end. In some embodiments, the conical section comprises pores. In some embodiments, the second diameter is smaller than the first diameter.

In some embodiments, an axial length of the conical section is between about 1 cm and about 5 cm. In some embodiments, the conical section slopes radially inwardly at an angle of between about 33 degrees and about 75 degrees. In some embodiments, the pores comprise a diameter of between about 0.5 mm and about 7 mm. In some embodiments, the pores comprise a diameter of between about 3 mm and about 5 mm. In some embodiments, the second diameter that is between about 25% and about 75% of the first diameter. In some embodiments, the second diameter is greater than the diameter of each of the pores.

In some embodiments, a method of collecting organisms on transport media is provided. The method can comprise contacting a biological sample with sample transport media. In some embodiments, the transport media comprises at least about 50% glycerol. In some embodiments, the transport media comprises at least about 5% of a mucolytic agent. In some embodiments, the infectious organism transport media does not include any additional infectious organism growth agent. The method can comprise sending the sample to a laboratory for culturing.

In some embodiments, contacting the biological sample comprises placing the biological sample in a transport tube comprising the sample transport media, a screen, and a sampling brush.

In some embodiments, a method of culturing organisms on transport media is provided. The method can comprise receiving a biological sample associated with transport media. In some embodiments, the transport media comprises at least about 50% glycerol. In some embodiments, the transport media comprises at least about 5% of a mucolytic agent. In some embodiments, the infectious organism transport media does not include any additional infectious organism growth agent. The method can comprise incubating the biological sample to culture one or more organisms.

In some embodiments, the method can comprise identifying the one or more cultured organisms. In some embodiments, the cultured organisms comprise bacterial organisms. In some embodiments, the cultured organisms comprise viral organisms. In some embodiments, the cultured organisms comprise fungal organisms. In some embodiments, the cultured organisms comprise parasitic organisms. In some embodiments, the one or more cultured organisms is selected from the group consisting of: Haemophilus influenzae, Klebsiella pneumoniae, Acinetobacter baumannii, aeruginosa, Stenotrophomonas maltophilia, Streptococcus pneumonia, Moraxella catarrhalis, Serratia marcescans, Pasteurella multocida, Group G streptococcus, Citrobacter freundii, Enterobacter aerogenes, Proteus mirabilis, extended-spectrum beta-lactamase producing Enterobacteraciae, methicillin-resistant Staphylococcus aureus, multi-drug resistant Streptococcus pneumoniae, Helicobacter pylori, Mycobacterium tuberculosis, Mycobacterium avium-intracellulare, other mycobacterium, and vancomycin-resistant Enterococcus. In some embodiments, the cultured organisms can be identified within about 36 hours after incubation or after sample collection. In some embodiments, the cultured organisms can be identified within about 24 hours after incubation or after sample collection. In some embodiments, the method can comprise freezing and thawing the biological sample, wherein the biological sample is frozen and thawed while preserving cellular wall integrity. In some embodiments, the method can comprise incubating the sample at a desired temperature for up to 24 hours in order to increase the density of bacteria in samples with low initial bacterial density at collection. In some embodiments, the desired temperature is about 37° C. In some embodiments, the method can comprise performing antimicrobial sensitivity studies on the cultured organisms.

In some embodiments, a biological transport system is provided. The biological transport system comprises any number of features disclosed herein.

In some embodiments, a method of culturing organisms on transport media is provided. The method comprises any number of features as disclosed herein.

BRIEF DESCRIPTION OF THE DRAWINGS

FIGS. 1L-1O illustrates comparative examples of conventional culture processing compared with prophetic specimen collection, according to some embodiments of the invention.

DETAILED DESCRIPTION

Figure 1A:
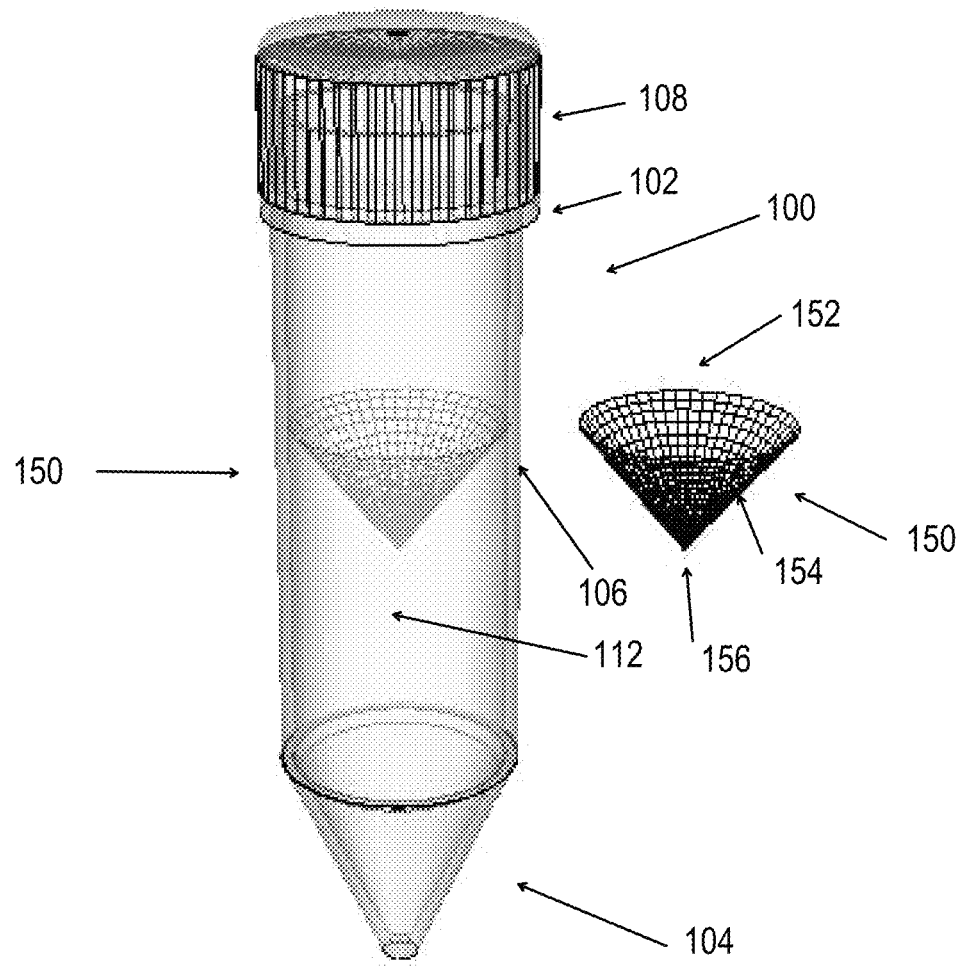
FIGS. 1A-1H illustrates embodiments of a laboratory transport tube including an axially-movable screen.

Disclosed herein is an improved system and method for transporting biological samples, including a unique transport medium and homogenization device configured to protect bacterial viability which greatly enhances diagnostic accuracy over current techniques, and an improved collection tube including an integrated collection screen, collection brush, and an improved transport case. The systems and methods allow samples to be frozen and thawed while preserving cellular wall integrity during transport or storage, and furthermore can preserve the survival of the bacterial sample which dramatically increases the ability of the lab to correctly identify the infectious agent in a quick and expeditious manner. In some embodiments, growth of any number of organisms as disclosed herein can be sufficient for identification and/or sensitivity to antimicrobials within about 72, 60, 48, 42, 36, 30, 24, 18, 12 hours, or even less.

Some systems and methods as disclosed herein can include any number of the following advantages: the transport media preserves the survival of the bacterial sample which dramatically increases yield of the infectious agent, and thus the ability of the lab to correctly identify the infectious agent; breaks down protective bacterial barriers and biofilms which immediately exposes the organisms to a nutritive broth which encourages growth and reproduction; promotes the even distribution of some or all active organisms in its low viscosity solution which increases the probability the lab will transfer the organism from sample to culture plate, thereby increasing the chance that the lab will identify the infectious agent; increases the chance that even the most vulnerable infectious bacteria will survive outside the body long enough to be cultured in the lab; enables samples to be frozen for long term storage or transport; samples can travel great distances without losing the viability of the organisms collected; reintroduces the lost art of the bedside culture by enabling practitioners to collect samples directly into our culture media with minimal to no changes to current protocols; and/or exhibits a better identification process of infectious organisms in a sample that also contains benign colonizing bacteria than current PCR genetic techniques. Furthermore, systems and methods as disclosed herein can provide clinicians and healthcare organizations with faster and more accurate culture results. This point alone can differentiate any reference laboratory from other labs in the same market.

In some embodiments, systems and methods as disclosed herein can enhance the laboratory/client relationship by indirectly improving reimbursement and compliance with clinical quality measures. In some embodiments, systems and methods can also directly benefit labs by developing competitive clinical and technological advantages in any given market through the above examples. Furthermore, systems and methods can increase potential revenue by providing accurate culture results. Accurate results lead to the use of specific codes which result in higher reimbursement rates and to the streamlining of antibiotic therapy which typically will reduce the cost to hospitals, and more importantly, reduce harm to patients. Systems and methods, including transport tubes as disclosed herein can be compatible with automated plating and culture systems, and also speed up the process as a technician is not required to open the specimen to add additional reagents. This also helps protect lab personnel from infection by aerosolized organisms. Furthermore, some labs utilize a mucolytic agent after the sample arrives in the lab. This can add 1-6 hours or more to the workup of the sample due to the time required to digest the sample. This can also increase the risk that the sample is not fully digested due to excessive waiting and forces the technologist to plate the sample without mucolysis. Systems and methods as disclosed herein can advantageously allow for digestion of sputum samples by mucolytic agents in transport, there is no downtime waiting for the sample to digest when it arrives, and all mucolytic therapy is done in the transport media, and none thereafter in some embodiments. Furthermore, conventional methods of using mucolytic agents on arrival involve the transfer of a small amount of the sputum sample to a separate tube containing the mucolytic agent. This can compound the sample error, because the sputum sample is not homogenized in toto. As only a small amount is selected, this can exclude pathogens present in a portion of the sample not selected.

In some embodiments, disclosed is an infectious organism transport media comprising about glycerol (glycerin) and a mucolytic agent, or other agent to reduce the viscosity of the biological sample. In some embodiments, the mucolytic agent could include, for example, one or more of Dithiothreitol (DTT, also known as Sputolysin®) (by weight/weight percentage in some cases), Dithiocrythritol (DTE); Cysteine (Cys), Tris 2-carboxyethyphosphine (TCEP), N-Acetyl-L-Cysteine (NAC), nacystelyn, dornase alfa, thymosin B4, heparin, and/or or others, without any other nutrient media, or substantially without any other nutrient media. In some embodiments including both glycerol and additional nutrient media, the glycerol concentration is at least about 90%, 95%, 96%, 97%, 98%, 99%, 99.5%, 99.9%, or more with respect to the total volume of nutrient media (e.g., glycerol plus other nutrient media). The mucolytic agent, e.g., Sputolysin® (Dithiothreitol) for example, could be in liquid, powder, and/or other forms. Prior to the present invention, it was widely believed that additional nutrient/growth media (other than glycerol) including additional gases such as methane or other gases would be required to allow for the maintenance of the pathogens during transport. Prior publications are known that disclose a lower concentration of glycerol (15-45%), but also require the glycerol to be in combination with conventional bacterial growth media. In some embodiments, the concentration of glycerol in a transport media can be much higher, such as about or at least about 60%, 65%, 70%, 75%, 80%, 81%, 82%, 83%, 84%, 85%, 86%, 87%, 88%, 89%, 90%, 91%, 92%, 93%, 94%, 95%, or more, or ranges including any two of the foregoing values, such as between about 85% and about 95% in some cases. In some embodiments, the glycerol concentration can be any concentration, including a lower concentration, such as between about 10% and about 50%, between about 15% and about 45%, between about 10% and about 95%, or other ranges including any two of the values disclosed herein for example so long as no other nutrient media is present (concentrations herein listed as % by volume of the entire media; as one non-limiting example, 10 mL of media can include 7 mL of glycerol (70% concentration of the media), 2 mL of Sputolysin® (Dithiothreitol) (20% concentration of the media), and 1 mL of sterile water (10% concentration of the media)).

In some embodiments, the concentration of mucolytic or other viscosity reducing agent, could be, for example, about, at least about, or no more than about 5%, 6%, 7%, 8%, 9%, 10%, 11%, 12%, 13%, 14%, 15%, 16%, 17%, 18%, 19%, 20%, 25%, 30% or more, or ranges including any two of the foregoing values, such as between about 5% and about 15% in some cases (concentrations listed as % by weight of the entire media).

In some embodiments, a fluid, such as sterile distilled water for example, can be added to the media (e.g., glycerol-sputolysin media) in any combination as needed to lower the viscosity of the sample. In some embodiments, the fluid can be add such that the amount of fluid in the media is about, at least about, or no more than about 1%, 2%, 3%, 4%, 5%, 6%, 7%, 8%, 9%, 10%, 15%, 20%, 25%, 30%, 35%, 40%, 50%, or more or less % by weight of the media.

Not to be limited by theory, glycerol by itself can surprisingly and unexpectedly function to attenuate the overgrowth of a bacterial culture by, for example, fungi or yeasts. Fungi and yeasts are colonizers of many anatomic locations. When a sample is taken, these colonizers are naturally entrained into the sample and naturally become part of the diagnostic culture. When present in overabundance, fungi and yeasts will overgrow the plate obscuring visibility of pathogenic bacteria rendering accurate diagnosis difficult to impossible.

Furthermore, the high concentration of glycerol in some embodiments of the transport media as disclosed herein can facilitate freezing of the original obtained sample instead of having to culture out bacteria, then freeze the sample. Additional potential non-limiting advantages include allowing for future research on non-bacterial components of the sputum such as antibodies, interferons, cells such as lung cells, and the like, and allowing for agitation of the sample in the field and exposure of the sample to the nutritive broth and allow for immediate (no additional step) centrifugation of the sample.

In some embodiments, the media does not include any conventional microbiological media such as MacConkey agar medium, Hekoten enteric agar medium, mannitol salt agar medium, xylosine lysine deoxycholate medium, Baird-Parker agar medium, Columbia broth, trypticase soy broth, Todd-Hewitt media, Mueller-Hinton broth, brain heart infusion broth, tiogycolate broth, Stuarts medium, Amies medium with or without charcoal, Cary and Blair medium, chocolate agar medium, and/or *Brucella* broth. In some embodiments, the media does not include milk, such as dry non-fat milk. Limiting (e.g., eliminating) use of these agents, especially those derived from animal products, can facilitate international transport since there are no unregulated animal or dairy products used for specimen transport.

Systems and methods as disclosed herein can be used to store a wide variety of biological samples, including but not limited to sputum, blood, serum, plasma, urine, stool, bile, wound, skin, oral, nasal, gastric, intestinal, rectal, vaginal, cervical, urethral, cerebrospinal fluid, pleural fluid, peritoneal fluid, joint fluid, organ biopsy samples, and the like. The samples could be from a human individual, a mammal or other animals. The samples could also include environmental samples not from an animal, such as from food, beverages (including alcoholic and non-alcoholic beverages), water, soil, clothing, building materials, and the like. In some embodiments, the samples do not just include microbes per se, but biological samples for diagnosis of a clinical or other specimen. In some embodiments, the systems and methods do not involve an additional gas supply, such as methane gas for example.

Systems and methods as disclosed herein can be used to ensure survival time of the biological specimen of interest for about or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 45, 60, 75, 90 days, or more, or ranges including any two of the foregoing values. The specimen of interest could include bacterial, viral, fungal, and/or parasitic specimens. The bacterial specimens could include, for example, gram positive, gram negative, anaerobic, or acid-fast bacteria, among others. The specimen of interest can also include fungus/yeast, such as *Candida* for example. The bacterial specimens could also be atypical bacteria, including but not limited to *Chlamydiaceae, Legionella* and the *Mycoplasmataceae* (including *Mycoplasma* and *Ureaplasma*); the Rickettsiaceae are also often considered atypical. Bacterial specimens could be aerobic or anaerobic.

In some embodiments, the specimen of interest can be frozen at a temperature of about or no more than about 0° C., −10° C., −20° C., −30° C., −40° C., −50° C., −60° C., −70° C., −80° C., −90° C., −100° C., or ranges including any two of the foregoing values.

In some embodiments, the samples can be placed into contact with the glycerol and mucolytic or other viscosity-reducing agent either together or separately. The sample mixture can be shaken once placed into a container, in some cases. In some embodiments one part sample can be mixed with between about 1 part to about 100 parts of transport media, such as about 1:100, 1:50, 1:25, 1:20, 1:10, 1:5, 1:4, 1:3, 1:2, 1:1 of sample: transport media, or ranges including any two of the foregoing values.

In some embodiments, the samples can be placed into any appropriate transport device. In some embodiments, also disclosed herein is a laboratory transport tube 100 comprising an axially-movable screen 150, as illustrated in FIG. 1A. The tube 100 can include a first open end 102, a second closed end 104, and an elongate body 106 there between that can be tubular as shown. The open end 102 can be configured to house a cap 108 thereon to isolate the sample therein. The cap 108 can be attachable to the open end 102 via complementary threads, friction fit, snap-on tabs, or other locking mechanisms. The cap 108 can also include ridges or other surface features as shown for ergonomic gripping while twisting and untwisting the cap 108. The elongate body 106 can have a channel 112 therein, and include a section with a relatively constant diameter as shown, and be configured to house a screen or filter element 150 within the channel 112, that can be conically shaped as shown with a larger top diameter and a smaller bottom diameter, with an open top end 152, a sidewall 154 including a plurality of holes or pores, and a bottom end 156. The screen 150 can be fixed in place, or axially movable toward the closed end 104 of the transport tube 100, which can take substantially mirror the geometry and diameter of the screen 150 as illustrated (e.g., a conical bottom end) that can be integrally formed together as one solid design, or bonded or otherwise attached in place to the elongate body 150. In some embodiments, the screen 150 can be fixed in place along the elongate body 106, such as via friction fit, adhesives, barbs, a flange extending radially inward from the inner diameter of the elongate body 106, and the like. The screen 150 can be conically-shaped as illustrated (e.g., entirely conically shaped), or other shapes, including a cylindrical shape, flat disc, or other shapes, or including combinations thereof. The screen 150 can include several advantages, including any number of the following: assisting with infection control (no backsplash) when the biological sample is placed into the transport tube; assisting with agitation of the sample in the field to ensure appropriate mixing and dispersion of bacteria throughout the broth; breaking up any biofilms and facilitating mucolytic activity of a reducing agent; allowing for greater oxygen dissolution in the broth to assist pathogens with aerobic respiration; allowing the sample can be centrifuged if desired without removal of the screen; and/or can help break down biofilms on surgical samples/prosthetics to allow bacteria to enter into exponential growth phase and reduce risk of no growth in culture (common with, for example, bone samples/prostheses). In some embodiments, the screen can be integrally formed and manufactured with the transport tube itself (e.g., via 3D printing or other techniques).

Figure 1B:
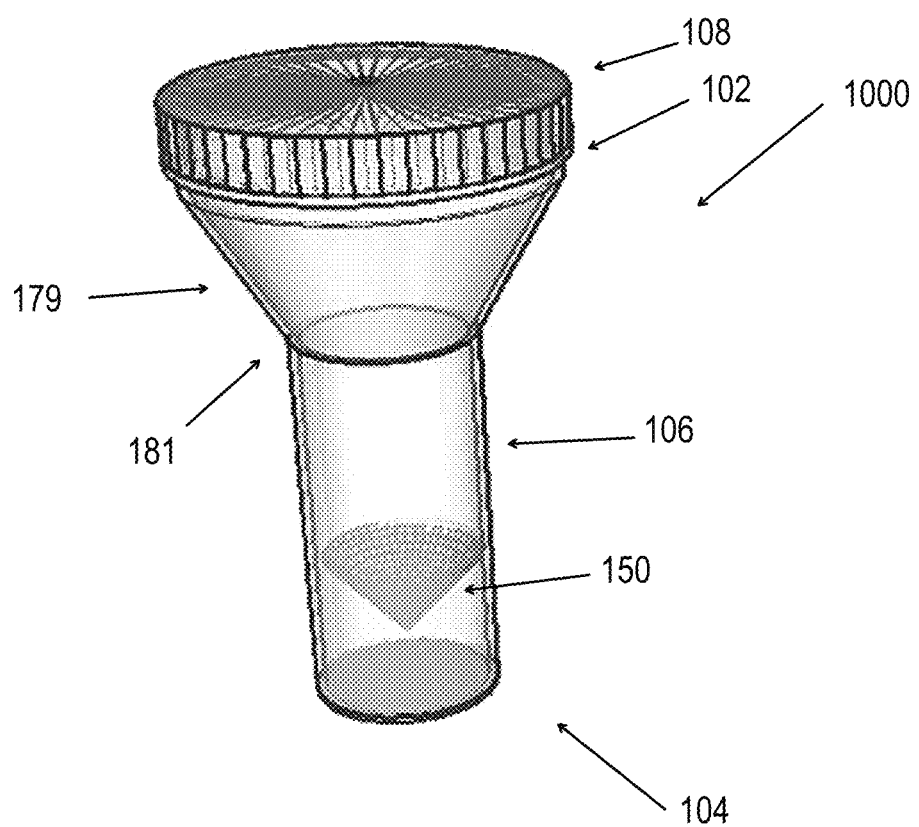

FIG. 1B illustrates an embodiment of a transport tube 1000 that can include any number of features of FIG. 1A for example, except for the presence of a wide-mouth open end 102 with a diameter greater than that of the closed end 104. A frustoconical section with a tapering diameter 179 from top to bottom can be directly connected at transition point 181 to a more distal tubular section with a diameter smaller than that of the open end 102. The frustoconical/funnel section and tubular section can be integrally formed together as one solid design, or otherwise bonded or attached together in other embodiments. In some embodiments, the open end diameter can be about, at least about, or no more than about 25%, 50%, 75%, 100%, 125%, 150%, 200%, or more or less than that of the closed distal end of the tube, or ranges including any two of the foregoing values. In some embodiments, the wide-mouth open end can have a diameter of between about 4 cm and about 8 cm, or between about 4 cm and about 5 cm. In some embodiments, the tubular section can have a diameter of between about 1 cm and about 4 cm, or between about 2 cm and about 3 cm. In contrast to the embodiment shown in FIG. 1A, the closed end 104 of the tube 1000 can have a flat bottom wall rather than the conical distal end shown in FIG. 1A.

Figure 1C:
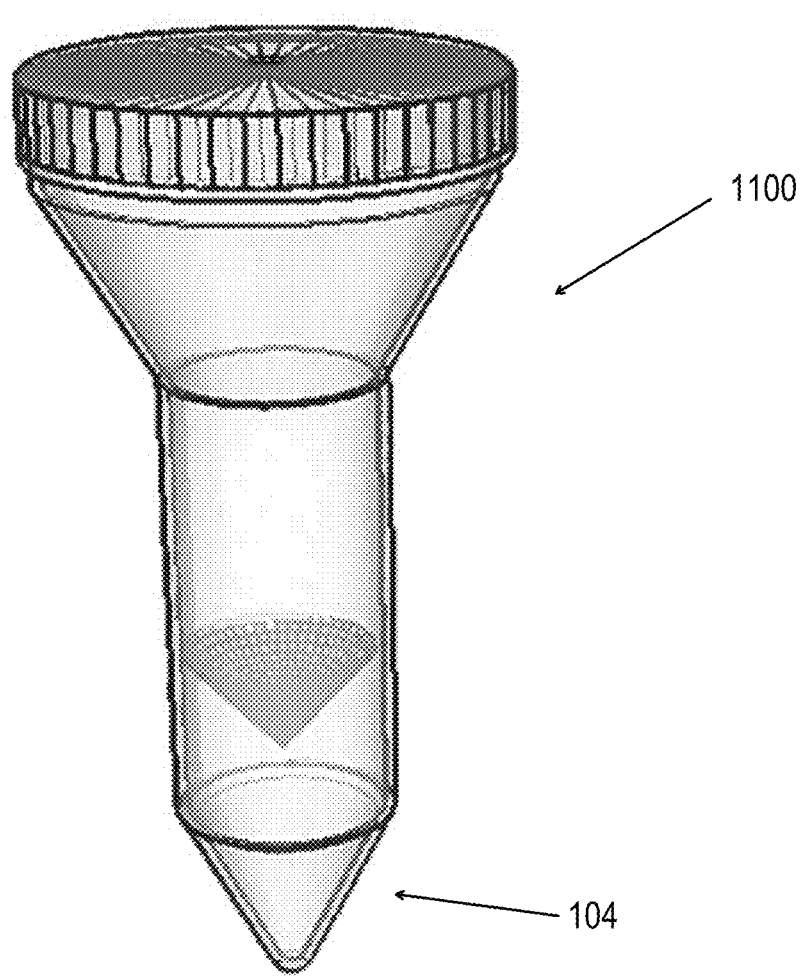

FIG. 1C illustrates an embodiment of a transport tube 1100 that can be similar to that of FIG. 1B, except for the presence of a conical closed distal end as shown in FIG. 1A.

Figure 1D:
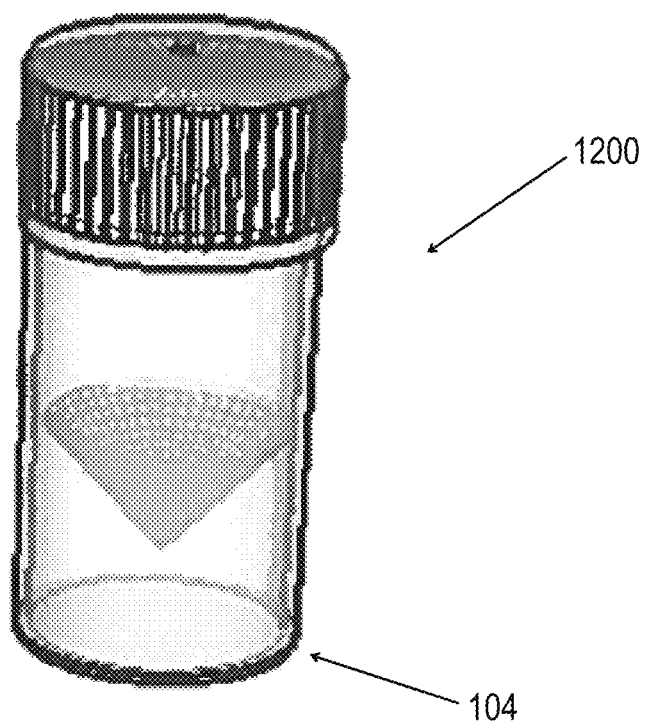

FIG. 1D illustrates an embodiment of a transport tube 1200 that can be similar to that of FIG. 1A for example, except the closed end of the tube 1000 can have a flat bottom wall similar to as shown in FIG. 1B for example.

Figure 1E:
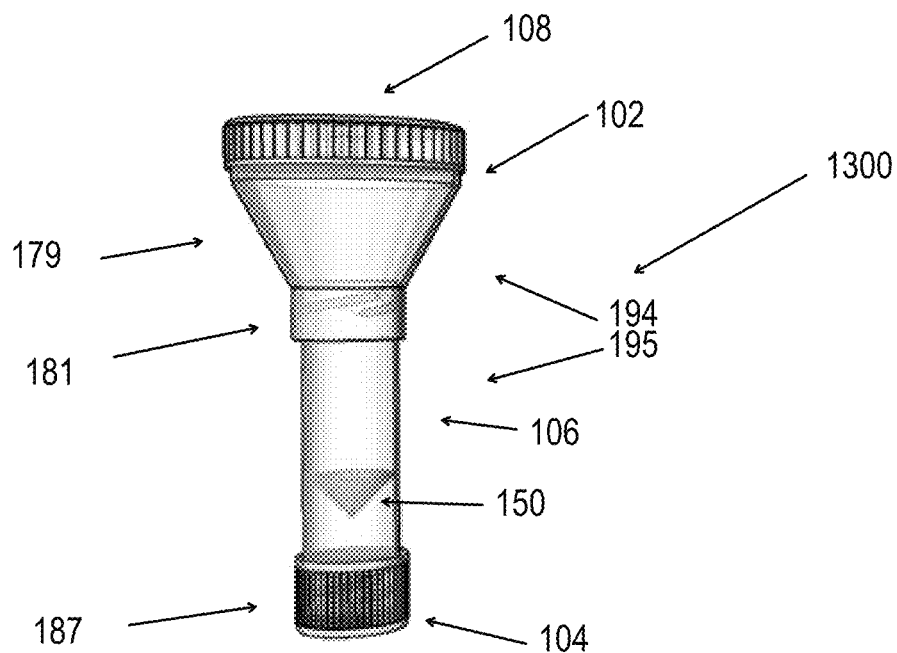
Figure 1F:
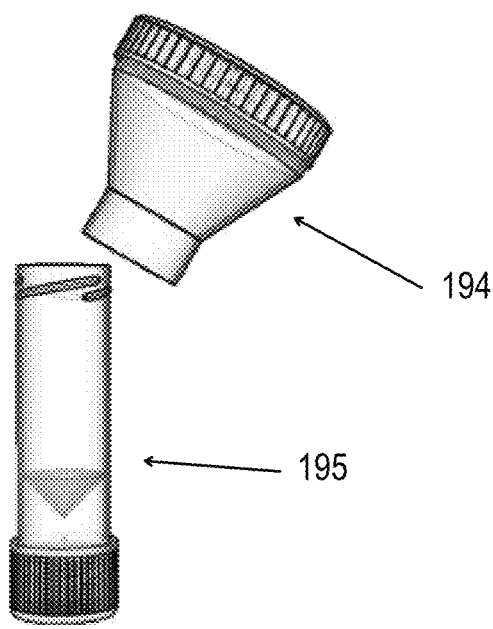
Figure 1G:
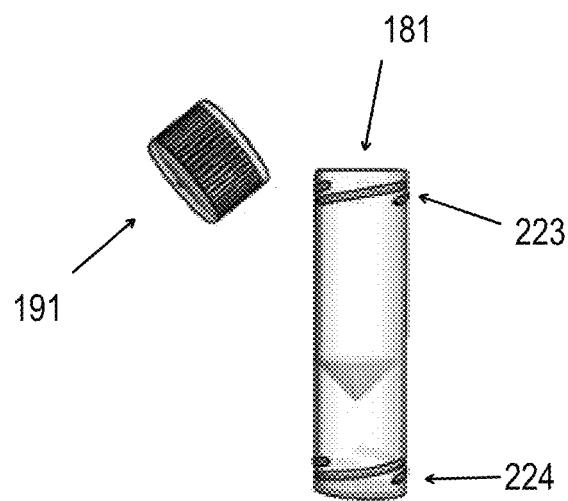
Figure 1H:
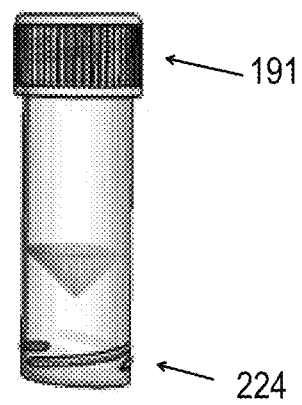

FIG. 1E illustrates an embodiment of a biological specimen container 1300 that can be similar to that of FIG. 1B for example, including wide-mouth open end 102, cap 108, and frustoconical/funnel section with a tapering diameter 179 from top to bottom to transition zone 181, which can have a narrower diameter with a, for example, cylindrical cross-section as shown. However, the upper section 194 above 181 can be removably attachable and detachable to lower section 195 including the elongate body 106 via complementary threads, friction fit, snap-on tabs, or other locking mechanisms. Also, the second end 104 can be an open end (rather than a closed end as shown in FIGS. 1A-1D), and reversibly closable via cap 187. In other words, a transport tube 1300 can be removably capped at both ends, and attachable and/or detachable at an intermediate axial location along the specimen container as well. Such an embodiment can be advantageously utilized for expectoration or collection of any sample material that may benefit from funneling. The upper cap 108 can be removed, and the sample material funneled in through the top end 102, passing through narrowing diameter frustoconical/funnel section 179, past transition zone 181, and into elongate body 106 and optionally through screen 150 as previously described. Once the sample moves in the lower section 195 (e.g., the transport tube proper), the funnel upper section 194 can be detached (e.g., by unscrewing upper section 194) as illustrated in FIG. 1F, and replaced by a cap 191 (which can be smaller diameter than the cap 108 for the wide-mouth detached open end 102) on the "new" top end where the previous transition zone 181 was, as shown schematically in FIGS. 1G and 1H, also showing threads 223, 224 proximate both ends on the outer sidewall of the lower section 195 (transport tube proper).

In some embodiments, a transport tube could include an outer diameter or inner diameter at the top end, bottom end, and/or intermediate axial portion of between about 1 cm and about 10 cm, between about 2 cm and about 5 cm, between about 2 cm and about 4 cm, or between about 2 cm and about 3 cm, such as about 1 cm, 1.5 cm, 2 cm, 2.5 cm, 3 cm, 3.5 cm, 4 cm, 4.5 cm, 5 cm, 5.5 cm, 6 cm, 6.5 cm, 7 cm, 7.5 cm, 8 cm, 8.5 cm, 9 cm, 9.5 cm, 10 cm, or more or less, or ranges including any two of the foregoing values. Some embodiments can include larger sizes to meet customized culture requirements, e.g., large prostheses. In some embodiments, a screen can have a fenestration/pore size of between about 0.5 mm and about 5 mm, such as about 0.5 mm, 1 mm, 1.5 mm, 2 mm, 2.5 mm, 3 mm, 3.5 mm, 4 mm, 4.5 mm, 5 mm, or more or less, or ranges including any two of the foregoing values. In some embodiments, the pore size can be configured to take into account the viscosity of the biological sample. The screen, in some embodiments, could have an open top end diameter of between about 2 cm and about 8 cm, between about 2 cm and about 4 cm, or between about 2 cm and about 3 cm, such as about 2 cm, 2.5 cm, 3 cm, 3.5 cm, 4 cm, 4.5 cm, 5 cm, 5.5 cm, 6 cm, 6.5 cm, 7 cm, 7.5 cm, 8 cm, or more or less, or ranges including any two of the foregoing values. In some embodiments, there is a ratio of pore to solid material surface area, where the pore surface area to the solid surface area is about 5:1, 4:1, 3:1, 2:1, 1:1, 1:2, 1:3, 1:4, 1:5, 1:6, or more or less, or ranges including any two of the foregoing values. In some embodiments, the pore surface area is less than half the solid surface area of the screen. In some embodiments, the pore surface area is less than a quarter of the solid surface area of the screen. In some embodiments, the pore surface area to the solid surface area ratio is between about 5:1 and 1:5, or between about 3:1 and 1:3, or between about 1:2 and 2:1. Other configurations are contemplated.

In some embodiments, a modular biological sample container is provided. The sample container can comprise an upper section comprising a first lumen configured to be reversibly closed with a first cap. The sample container can comprise a lower section comprising a second lumen configured to be reversibly closed with a second cap. The sample container can comprise a funnel portion proximate a top end of the upper section. The sample container can comprise a cylindrical portion proximate the funnel portion. The sample container can comprise a transition zone between the funnel portion and the cylindrical portion. The sample container can comprise reversible connectors configured such that the upper section can be reversibly attached and/or detached from the lower section.

The sample container can comprise a screen within the lower section. The first lumen can comprise a diameter greater than a diameter of the second lumen. The reversible connectors can comprise threaded surfaces. The threaded surfaces can comprise an inner sidewall of the upper section and an outer sidewall of the lower section. The sample container can comprise threaded surfaces proximate a top end of the upper section and a bottom end of the lower section. The second cap can be removably coupled to the bottom end of the lower section when the upper section is coupled to the lower section. A modular biological sample kit can be provided. The kit can comprise any container described herein. The kit can comprise a third cap configured to reversibly close the transition zone following detachment of the funnel portion from the cylindrical portion.

Figure 1I:
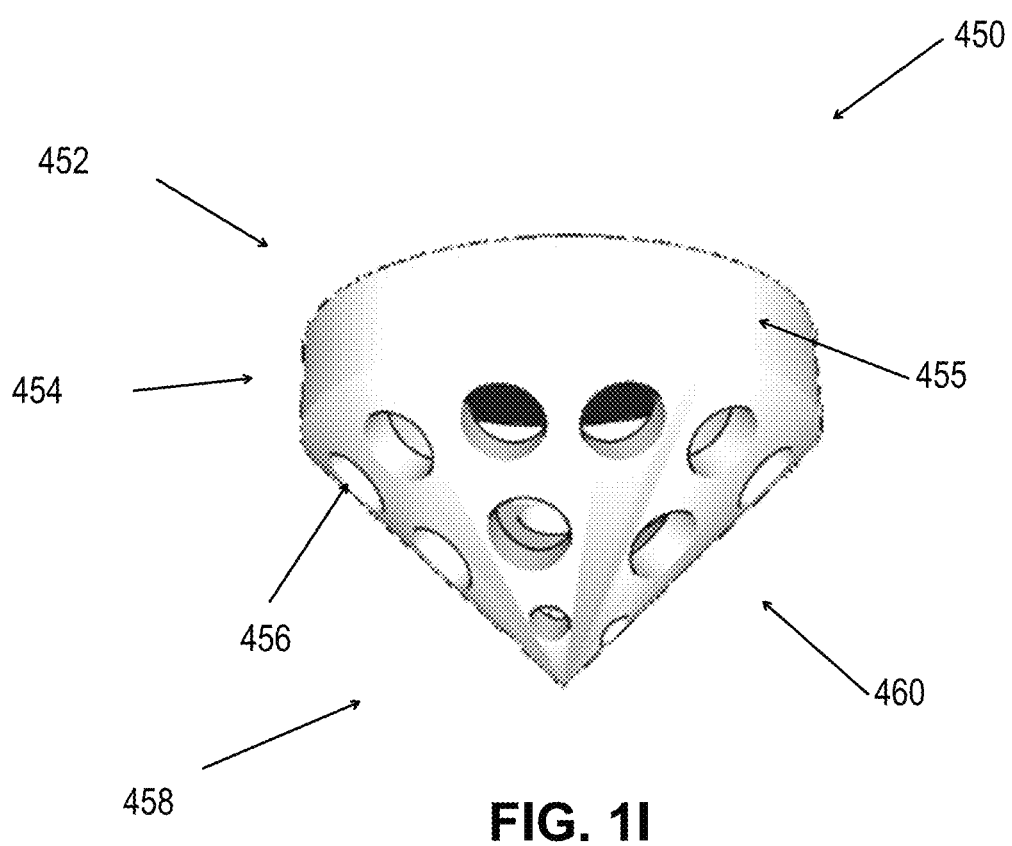
FIG. 1I illustrates another embodiment of a screen configured to be placed within a transport tube, with an upper cylindrical portion and a lower conical portion.

FIG. 1I illustrates another embodiment of a screen 450 including a top end 452 and a bottom end 460, with a cylindrical portion 454 proximate the top end 452 and a conical portion 458 directly adjacent to, and distal to the cylindrical portion 454. The cylindrical portion 454 can including fenestrations/pores 456 that can be as described, for example, elsewhere herein. The conical portion 458 could include fenestrations/pores, or not include any fenestrations/pores in other embodiments. In some embodiments, the cylindrical portion 454 includes a circumferential sidewall or rim 455 configured to sit against the inner diameter of the transport tube (not shown) to assist in stabilizing the screen 450 within the transport tube. In some embodiments, the cylindrical portion 454 has a dimension, such as an axial length and/or thickness, of between about 1 mm and about 4 mm in some embodiments, such as about 1 mm, 2 mm, 3 mm, 4 mm, or ranges including any two of the foregoing values. In some embodiments, the conical portion 456 can have an axial length of about 0.5 cm, 1 cm, 1.5 cm, 2 cm, 2.5 cm, 3 cm, or more or less, or ranges including any two of the foregoing values.

In some embodiments, a screen for a modular biological transport container can be provided. The screen can comprise a first open end comprising a first diameter. The screen can comprise a second open end comprising a second diameter. The screen can comprise a conical section comprising a sidewall defining a flow path between the first open end and the second open end. The conical section can comprise pores. The second diameter can be smaller than the first diameter. The axial length of the conical section can be between about 1 cm and about 5 cm. The conical section can slope radially inwardly at an angle of between about 33 degrees and about 75 degrees. The pores can comprise a diameter of between about 0.5 mm and about 7 mm. The pores comprise a diameter of between about 3 mm and about 5 mm. The second diameter can be between about 25% and about 75% of the first diameter. The second diameter can be greater than the diameter of each of the pores.

Figure 1J:
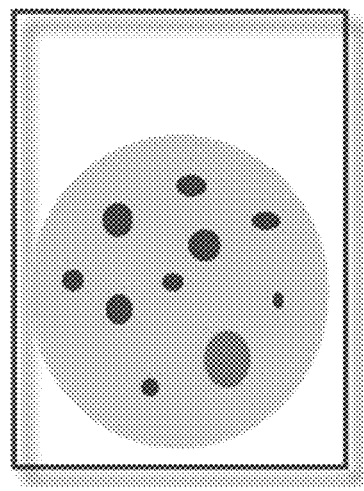
FIG. 1J schematically illustrates conventional specimen collection (e.g., a sputum sample collection) in a sterile plastic cup.
Figure 1K:
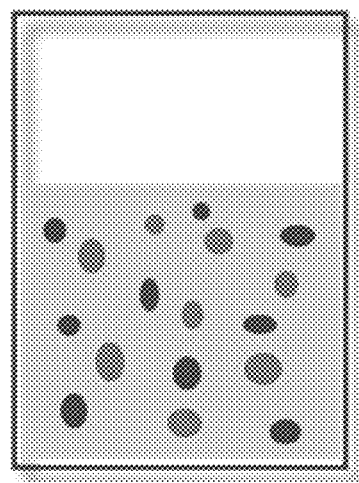
FIG. 1K illustrates specimen collection according to some embodiments of the invention, illustrating more even distribution of collected organisms within a sample which advantageously increases the chance that all organisms will be cultured.

FIG. 1J schematically illustrates conventional specimen collection (e.g., a sputum sample collection in a sterile plastic cup). As shown, the distribution of collected organisms is uneven, and there is a high chance that the lab will not collect the culprit infectious agents in a heterogeneous sample. This can be a hostile environment to infectious bacteria. FIG. 1K illustrates specimen collection according to some embodiments of the invention. Dissolution of sequestering debris and biofilms can occur, thereby exposing infectious organisms to the surprisingly nourishing glycerol medium, which can promote growth of collection organisms. More even distribution of collected organisms within a sample can advantageously increases the chance that all organisms will be cultured.

Figure 1L:
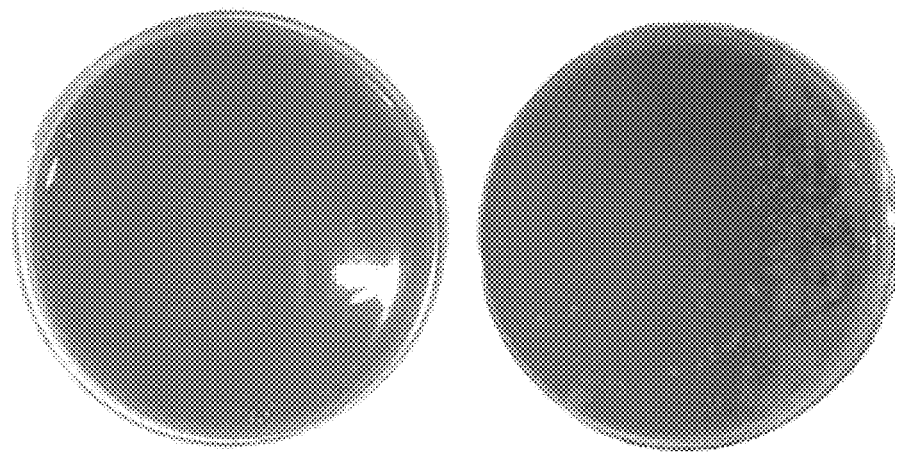

FIG. 1L illustrates one example of conventional culture processing compared with prophetic examples of specimen collection according to some embodiments of the invention. Transport systems and methods as disclosed herein can allow the infectious organisms to thrive after collection until it could be properly transported and plated in the microbiology lab. The left culture plate (conventional specimen collection) shows no growth, and the infectious organism was completely missed. However, the right culture plate is a prophetic example projecting that *H. influenzae* can be isolated and identified, enabling proper diagnosis and timely treatment. *H. influenzae* is a good example of an infectious bacteria that does not survive very long outside the respiratory system. It is a deadly cause of pneumonia and COPD exacerbations. Systems and methods as disclosed herein can improve *Haemophilus* diagnosis and timely treatment by promoting its growth and reproduction before plating for culture.

Figure 1M:
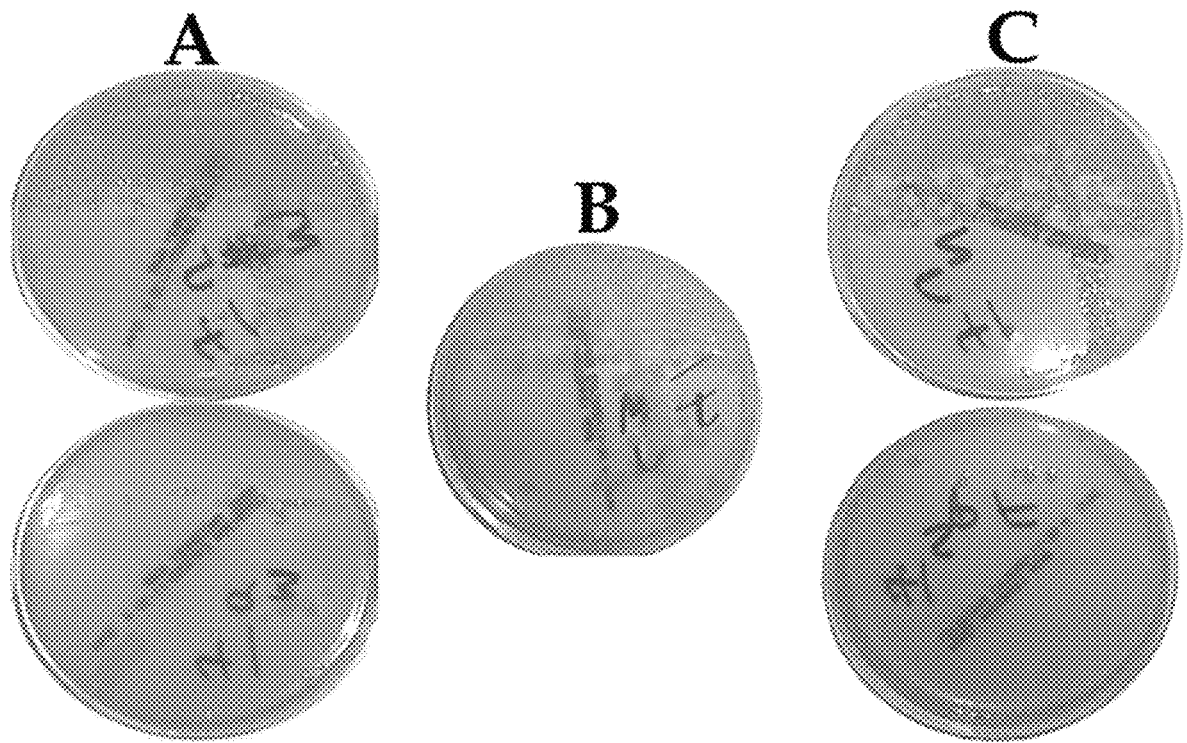

FIG. 1M illustrates further examples of conventional culture processing compared with prophetic examples of specimen collection including *Pseudomonas* and *Serratia* pathogens according to some embodiments of the invention. Column A illustrates samples collected and plated the same day (top plated is a prophetic example, bottom with conventional media). Column B illustrates a prophetic example sample refrigerated for several days, illustrating that the prolific growth can persist. Column C illustrates frozen samples (top plated as a prophetic example, bottom with conventional media) illustrating projected similar results to same day plating of Column A, even with freezing of the samples.

Figure 1N:
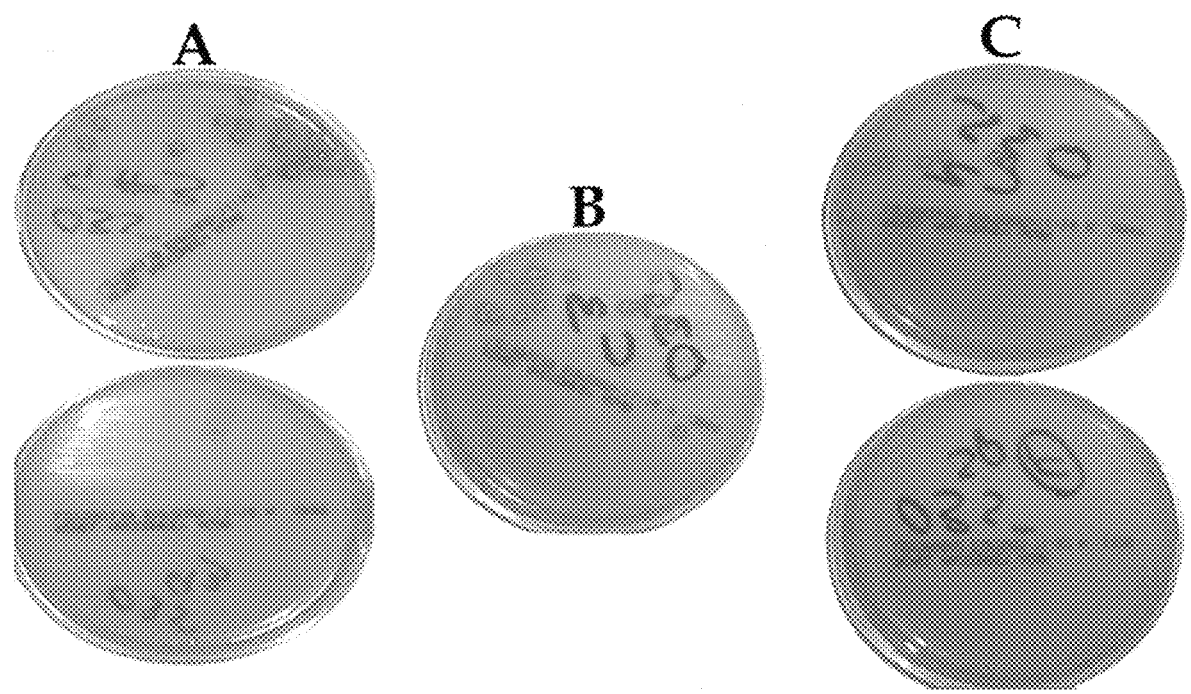

FIG. 1N illustrates further examples of conventional culture processing compared with prophetic examples of specimen collection including *Klebsiella* according to some embodiments of the invention. Similar to FIG. 1M above, Column A illustrates samples collected and plated the same day (top plated is a prophetic example, bottom with conventional media). Column B illustrates a prophetic example sample refrigerated for several days, illustrating that the prolific growth can persist. Column C illustrates frozen samples (top plated as a prophetic example, bottom with conventional media) illustrating projected similar results to same day plating of Column A, even with freezing of the samples.

As noted, systems and methods as disclosed herein can accurately identify the infectious agent compared to conventional collection techniques, even after the sample was frozen. The conventional collection methods often yield such a low amount of the infectious agent that the chance of not isolating the infectious pathogen is high. Conventional specimen collection can lead to antibiotic treatment that is not active against the infectious bacteria because the actual infectious agent is not able to be isolated. This leads to a failure of therapy, and associated morbidity and mortality risks, including septic shock, to the patient. The inventive embodiments as disclosed herein can improve yield in some cases utilizing a reducing agent, agitating the sample during transport, and the use of glycerol as disclosed herein.

FIG. 1O illustrates further examples of conventional culture processing compared with prophetic examples of specimen collection including Pneumococcus and *Moraxella* pathogens. The left plate illustrates growth on conventional media, which grew a single organism only, *Moraxella*. The right plate illustrates prophetic examples of growth with two distinct robust colonies of Pneumococcus and *Moraxella*. Pneumococcus is one of the most deadly forms of bacterial pneumonia and is often highly resistant to azithromycin among other antibiotic therapy given empirically for pneumonia in the outpatient setting. In this case the prophetic isolate is recovered and can be tested for antibiotic resistance. Inability to isolate can lead to treatment failure.

Some non-limiting examples of pathogens of which systems and methods as disclosed herein can improve detection of can include, but are not limited to, *Haemophilus influenzae, Klebsiella pneumoniae, Acinetobacter baumannii, Pseudomonas aeruginosa, Stenotrophomonas maltophilia, Streptococcus pneumonia, Moraxella catarrhalis, Serratia marcescans, Pasteurella multocida*, Group G *streptococcus, Citrobacter freundii, Enterobacter aerogenes, Proteus mirabilis*, extended-spectrum beta-lactamase producing *Enterobacteriacie*, methicillin-resistant *Staphylococcus aureus*, multi-drug resistant *Streptococcus pneumoniae, Helicobacter pylori, Mycobacterium tuberculosis, Mycobacterium avium-intracellulare*, other *mycobacterium*, vancomycin-resistant *Enterococcus*, and other bacterial and non-bacterial pathogens.

In an embodiment relating to *Helicobacter pylori* (associated with certain cases of gastritis, ulcers and gastric cancers), some non-limiting advantages include: recovery of gastric contents using a minimally invasive "string test" and immediate placement of these contents can allow transport and subsequent culture of the very fastidious *H. pylori* organism. The string test involves the collection of gastric and intestinal contents. The proximal end of a string is taped to the cheek of the subject and the remainder is swallowed and retrieved approximately 2 hours later. Culture of the organism now requires invasive endoscopy and biopsy. By using the present media following the string test, analysis of samples can be performed in a less invasive fashion in an outpatient clinics and antibiotic sensitivity can be tested as well. *H. pylori* has been cultured using systems and methods as disclosed herein utilizing a string test. It should be noted that the current methods of detecting *H. pylori* provide only a qualitative positive or negative result and there is no easy way to actually test the organism for antibiotic resistance. Culture is available, but frequently negative even if infection is strongly suspected or even seen on pathology. The present method would provide a convenient and less invasive method to culture the organisms so that testing for antibiotic resistance can be carried out.

Systems and methods as disclosed herein can be particularly advantageous, for example, with bone cultures, which conventionally are very difficult to grow and isolate causative pathogenic organisms from. For example, use of glycerol media, mucolytic, and/or agitation process with systems and methods as disclosed herein for example can unexpectedly and surprisingly grow out pathogens from bone samples. Furthermore, systems and methods can advantageously allow for transport, mucolysis, and digestion of endoscopy samples such as, but not limited to, gastric and duodenal brushing and biopsy samples. This can enhance recovery of *H. pylori*, for example.

Also disclosed herein is a storage and cooling system for sample collection tubes, particular useful for international/long-distance collection and research. The system can include a storage case including a plurality of wells configured to hold transport tubes and a unique transport cooling or freezing mechanism configured to sit in a Pelican case, and customized dry ice or foam refrigerant elements surrounding the storage case to cool the samples. Distinct from conventional sample cooling systems, the inventive storage case can be made to not only cool but to also secure and store while collecting. In addition, it is designed to transport by itself locally or within a Pelican case via any shipping method. The transport system allows for the collection of multiple samples over time while keeping them cold. The system is configured to fit into a Pelican case for easy standardized shipping as a "one stop" collection and shipping method. In some embodiments, a storage case can fit about 20, 30, 40, 50, 60, 70, 80, 90, 100, 110, 120, 130, 140, 150, 200, or more or less collection tubes, and ranges including any two of the foregoing values.

Figure 2A:
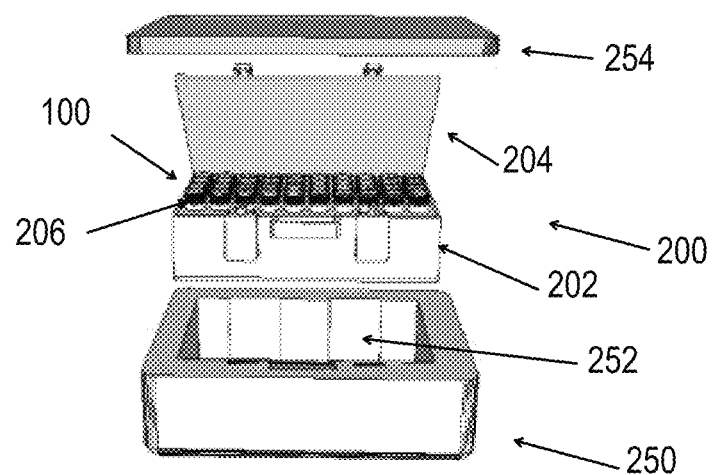
FIGS. 2A-2D illustrate embodiments of a storage and cooling system for sample collection tubes.
Figure 2B:
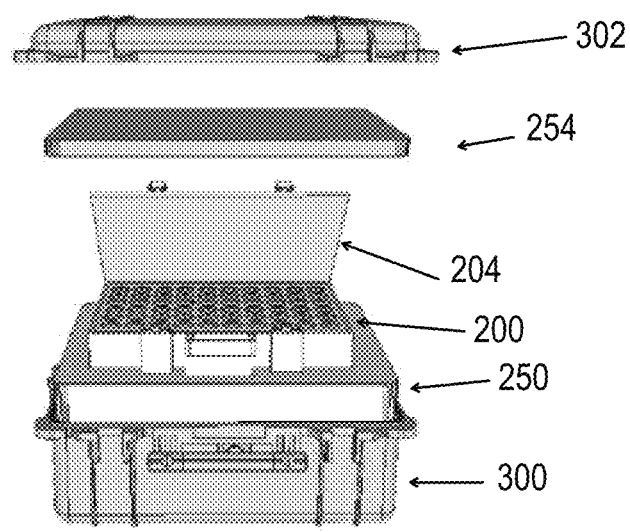
Figure 2C:
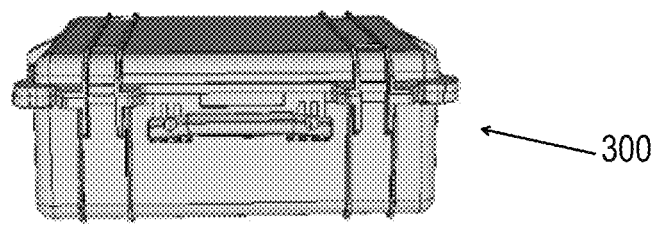
Figure 2D:
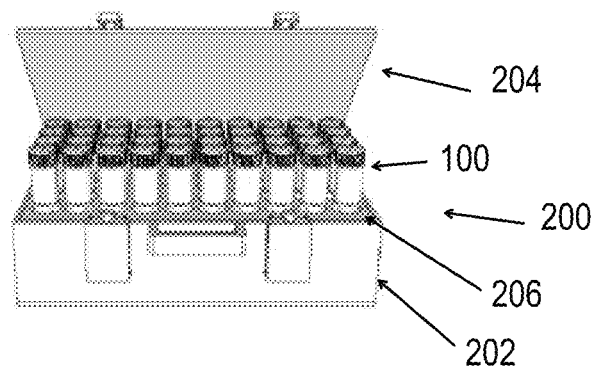

FIGS. 2A-2D illustrate embodiments of a storage and cooling system for sample collection tubes. FIG. 2A is an exploded view of a system including a storage case configured to fit in a cooling container. FIG. 2B is an exploded view of a system including a storage case configured to fit in a cooling container, which is in turn configured to fit in a Pelican case. FIG. 2C illustrates a closed Pelican case configured to fit the storage case and the cooling container of FIG. 2B. FIG. 2D illustrates that the storage case and the cooling container can be utilized independently of the Pelican case.

In some embodiments, the storage case 200 can include an outer shell 202, a movable lid 204, and an interior storage area with a plurality of wells 206 configured to fit sample containers, such as transport tubes 100 including those disclosed herein. The storage case 200 can be configured to fit within a cavity 252, such as a large central cavity 252 of a cooling container 250 that also includes a lid 254 configured to keep the cavity 252 closed and at a desired cool temperature for an extended period of time. The cavity 252 can be sized and configured such that custom-made dry ice, foam refrigerant pieces, or other cooling elements (not shown) can be placed around the storage case 200, and the cavity 252 also fits the storage case 200 therein. The storage case 200 within the cooling container 250 can be configured to be placed within a Pelican case 300 including a lid 302. In some embodiments, the storage case can be utilized independently of the cooling container and/or the Pelican case, and no cooling is required in some cases.

In some embodiments, an infectious organism transport system is provided. The transport system can comprise any transport media described herein. The transport system can comprise a transport tube. The transport tube can be any transport tube described herein. The transport tube can comprise a screen. The screen can comprise a conical screen. The screen can be axially movable. The transport tube can comprise a generally conical distal end. The transport tube can comprise a generally flat distal end. The transport tube can comprise an open end that comprises a diameter greater than that of a diameter of a more distal tubular portion of the transport tube. The transport tube can comprise an open end that comprises a diameter equal to that of a diameter of a more distal tubular portion of the transport tube. The transport tube can include any features described herein, or combination of features. The transport system can comprise a storage case comprising a plurality of wells configured to fit a plurality of transport tubes. The transport system can comprise a cooling container, the cooling container comprising a cavity configured to house the storage case therein. The transport system can comprise a Pelican case configured to house the cooling container therein.

In some embodiments, a method of transporting a biological sample is provided. The method can comprise collecting the biological sample from a subject. The method can comprise contacting the biological sample with a transport media. The method can utilize any transport media described herein. The transport media can comprise at least about 50% glycerol and at least about 5% of a mucolytic agent. The transport media does not include any additional growth media. The method can provide improved yield and/or diagnosis of the biological sample.

Contacting the sample with a transport media can comprise placing the biological sample within a transport tube. The transport tube can include any features described herein, or combination of features. The transport tube can comprise a screen. The screen can comprise a conical screen. The transport tube can comprise an integrated sampling brush. The method can comprise moving the conical screen to a closed distal end of the transport tube. The method can comprise transporting the biological sample to a sample diagnostic center. The method can comprise cooling the biological sample. The method can comprise shaking the biological sample prior to cooling. Cooling the biological sample can comprise freezing the biological sample. The method can comprise agitating the sample to homogenize the specimen prior to culture. The method can comprise incubating the sample at 37 degrees Celsius for up to 24 hours to increase the density of pathogenic bacteria prior to culture.

Figure 3A:
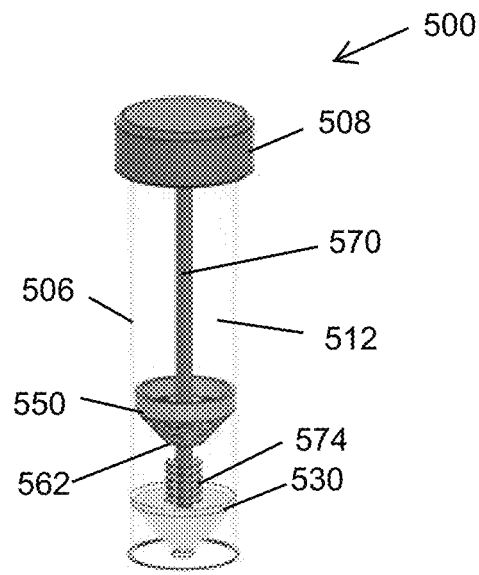
FIGS. 3A-3L illustrate embodiments of a laboratory transport tube including a screen and a sampling brush.
Figure 3B:
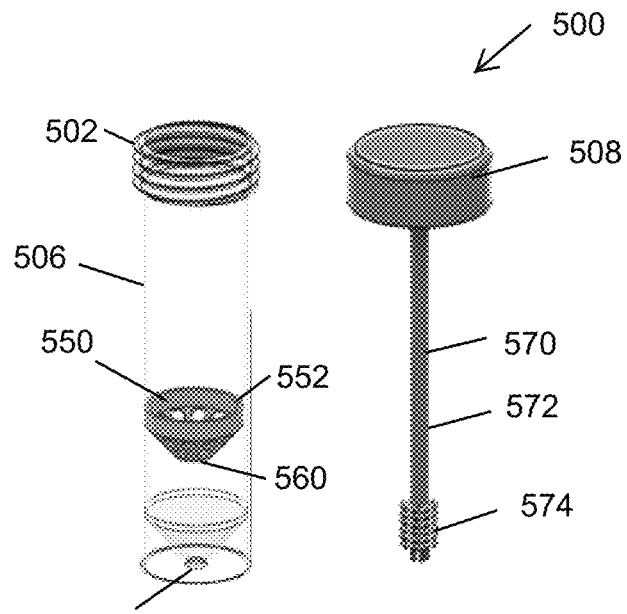

FIGS. 3A-3B illustrate embodiments of a laboratory transport tube 500. The laboratory transport tube 500 can include any of the features of any device, tube, or container described herein. The laboratory transport tube 500 comprises a screen 550. The screen can include any of the features of the screens described herein. The laboratory transport tube 500 comprises a sampling brush 570.

The transport tube 500 can include a first open end 502, a second closed end 504, and an elongate body 506 therebetween. The open end 502 can be configured to couple to a cap 508 which closes the tube. The cap 508 can be coupled to the open end 502 via any mechanical means including complementary threads, friction fit, snap-on tabs, or other locking mechanisms. The cap 508 can also include surface features for ergonomic gripping while coupling the cap 508 to the open end 502. The cap 508 and the open end 502 can be removably uncoupled to retrieve and utilize the sampling brush 570 during methods of use. In some embodiments, replacing the cap 508 will position the sampling brush 570 within the transport tube 500. The transport tube 500 can be reversibly closable.

In some embodiments, the second closed end 504 can have a flat bottom wall.

In some embodiments, the second closed end 504 can be formed of a cone 530. The cone 530 can be an insert or separately formed from the tube. The cone 530 can be integrally or monolithically formed with the tube. The cone 530 can facilitate sample collection by pooling the sample within the tube.

The elongate body 506 can have a channel 512 therein. In some embodiments, the elongate body 506 has a relatively constant diameter along the entire length. In other embodiments, the elongate body 506 has a relatively constant diameter along at least a portion of the length. The channel 512 is configured to house the screen 550. The channel 512 is configured to house the sampling brush 570.

Figure 3C:
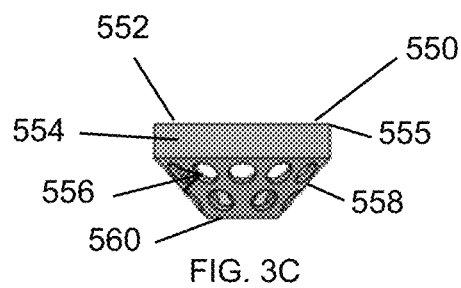
Figure 3D:
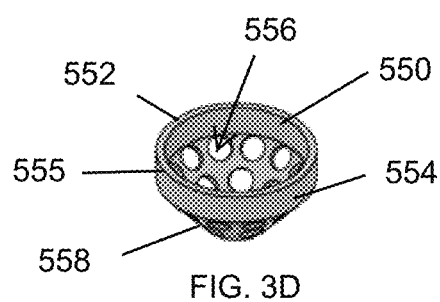
Figure 3E:
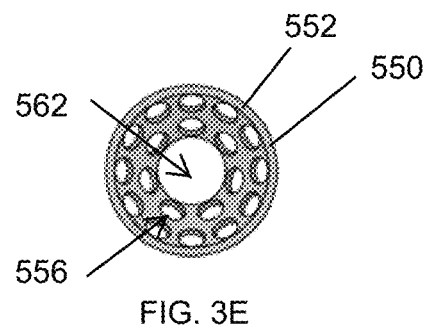
Figure 3F:
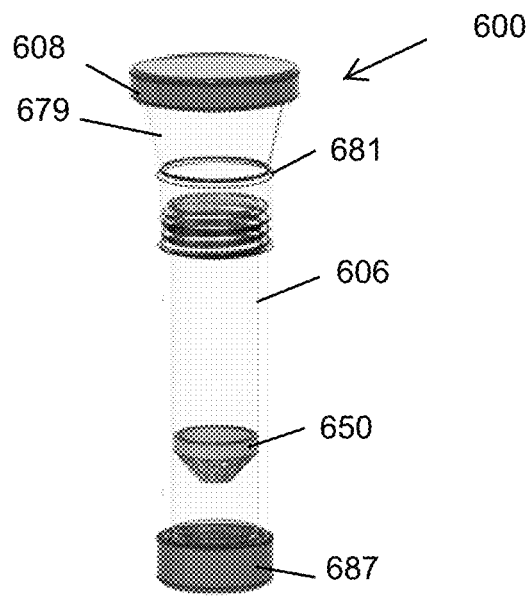
Figure 3G:
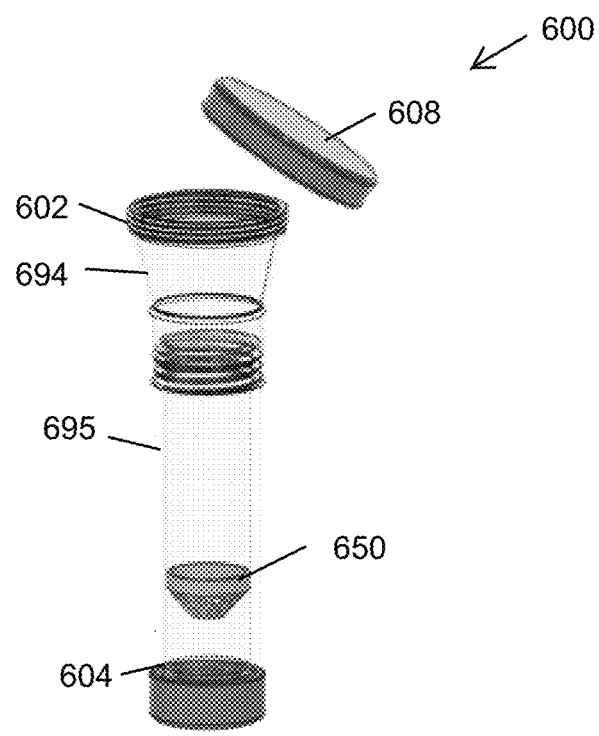
Figure 3H:
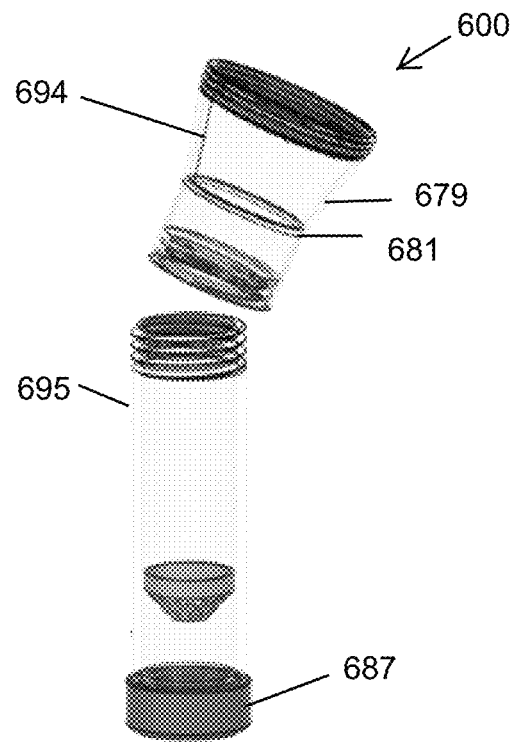
Figure 3I:
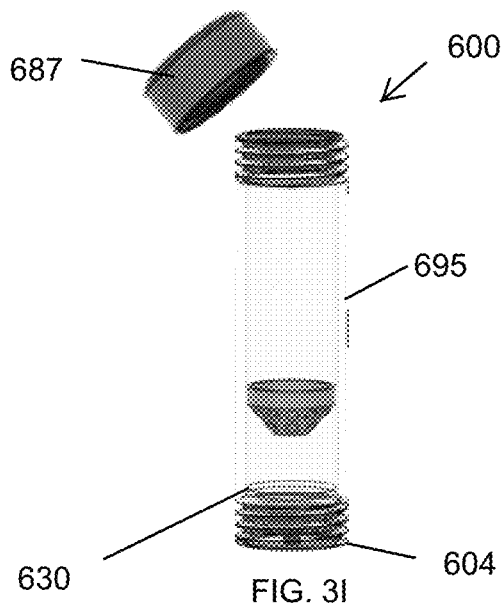
Figure 3J:
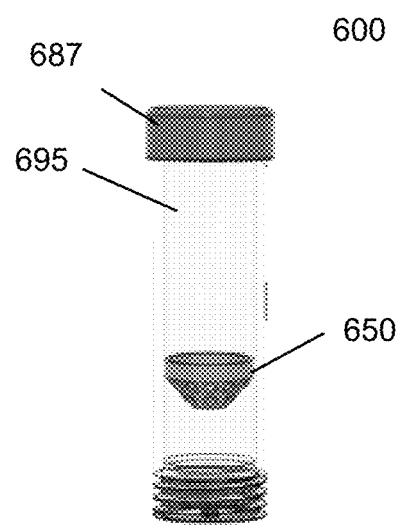

FIGS. 3C-3E an embodiment of the screen 550. The screen 550 can be used within the transport tube 500 or any device, tube or container described herein. The screen 550 can be fitted to and used in any existing or yet to be designed container.

The screen 550 can be conically shaped as shown with a larger top diameter and a smaller bottom diameter. The screen 550 can include at least one wall that tapers. In some embodiments, the screen 550 forms a point. In other embodiments, the screen 550 is truncated. The screen 550 can form a flattened surface. The screen 550 can include a top end 552 and a bottom end 560. The screen 550 can include a cylindrical portion 554 proximate the top end 552 and a conical portion 558 directly adjacent to, and distal to the cylindrical portion 554. The screen 550, or a portion thereof, can include a plurality of holes or pores 556. In some embodiments, the screen 550 can be fixed in place within the tube. The screen 550 can be fixed by any means including friction fit, interference fit, interlock, adhesives, barbs, a flange extending radially inward from the inner diameter of the elongate body 506, and the like. In other embodiments, the screen 550 is axially movable within the channel 512. While the screen 550 is shown as a conical shaped structure, other shapes are contemplated including a cylindrical shape, flat disc, or other shapes, or including combinations thereof.

In some embodiments, the superior rim 555 can form a circumferential or partially circumferential sidewall or rim. The superior rim 555 is configured to sit against the inner diameter of the transport tube 500. The superior rim 555 can assist in stabilizing the screen 550 within the transport tube 500. The superior rim 555 can be a cylindrical portion proximate the top end 552. The superior rim 555 can be a ridge or edge of the screen 550.

The screen 550 can include the conical portion 558 distal to the cylindrical portion 554. In some embodiments, the cylindrical portion 554 has a dimension, such as an axial length and/or thickness, of between about 1 mm and about 10 mm in some embodiments, such as about 1 mm, 2 mm, 3 mm, 4 mm, 5 mm, 6 mm, 7 mm, 8 mm, 9 mm, 10 mm, or ranges including any two of the foregoing values. In some embodiments, the conical portion 558 has a dimension, such as an axial length and/or thickness, of between about 1 cm and about 5 cm in some embodiments, such as about 0.5 cm, 1 cm, 1.5 cm, 2 cm, 2.5 cm, 3 cm, 4 cm, 5 cm, or ranges including any two of the foregoing values. In some embodiments, the conical portion 558 can have a slope angle of 33°-75°, such as 33°, 35°, 40°, 45°, 50°, 55°, 60°, 65°, 70°, 75°, or ranges including any two of the foregoing values. The slope angle can depend on the height and circumference.

The screen 550 can include a central hole 562. The screen 550 can be shaped to easily guide the sampling brush 570 through the central hole 562. The conical angle described herein is especially significant in automatic plating machines commonly used in labs across the country. The central hole 562 at the bottom end of the screen 550 can be between 8 mm and 12 mm, such as 8 mm, 9 mm, 10 mm, 11 mm, 12 mm, or more or less, or ranges including any two of the foregoing values. In some embodiments, the central hole 562 is 10 mm to accommodate commonly used swabs and loops.

The outside dimension of the screen 550 can vary to accommodate different sized containers. In some embodiments, the screen 550 can have outside diameter of between about 1 cm and about 4 cm, such as about 1 cm, 1.5 cm, 2 cm, 2.1 cm, 2.2 cm, 2.3 cm, 2.4 cm, 2.5 cm, 2.6 cm, 2.7 cm, 2.8 cm, 2.9 cm, 3 cm, 3.5 cm, 4 cm, or more or less, or ranges including any two of the foregoing values. In some embodiments, the screen 550 can have inside diameter of between about 1 cm and about 4 cm, such as about 1 cm, 1.5 cm, 2 cm, 2.1 cm, 2.2 cm, 2.3 cm, 2.4 cm, 2.5 cm, 2.6 cm, 2.7 cm, 2.8 cm, 2.9 cm, 3 cm, 3.5 cm, 4 cm, or more or less, or ranges including any two of the foregoing values. In some embodiments, the outside dimensions are 2.5 cm in diameter, inside dimensions are 2.3 cm.

The screen 550 can comprise a material that is able to withstand sterilization protocols such as autoclave, ionizing radiation, gamma radiation, ethylene oxide, ultraviolet germicidal irradiation (UVGI). The screen 550 can comprise High Heat PLA (3D870), High Heat PLA (3D850), High Heat PETG, Polypropylene (PP), Polymethylpentene (PMP), Polylactic acid (PLA), Polyacetal (Copolymer) (POM-C), Polyethylene terephthalate (PET), Polycarbonate (PC), Polycarbonate ABS alloy (PC-ABS), Polyetheretherketone (PEEK), Polyvinyl Chloride (PVC), Polyethylene (PE), Polyphenylsulfone (PPSU), High Temperature Resin, Glass infused Resin, SAE 316 stainless steel, SAE 316L stainless steel, SAE 440 stainless steel, SAE 420 stainless steel, any corrosion resistant steel, or glass, or any combination of these materials. The screen 550 can comprise any material that will not rust or substantially rust, corrode (for example, oxidize), or otherwise transform or degrade. The screen 550 can comprise any material that will not react to transport solution.

The transport tube 500 can include a device to track the tube. The device can be embedded within the tube. The device can include a Real Time Locating System (RTLS) by means of a bar code, RFID chip, GPS, WiFi, Bluetooth, Bluetooth Low Energy (BLE), or any combination of the aforementioned, or by means of any technology to track the tube. The transport tube 500 is compatible with automatic plating systems. The transport tube 500 is compatible with centrifuges. The transport tube 500 is such that it will be compatible with the transport containers described herein.

The transport tube 500 can include the sample brush 570. The sample brush 570 can include an elongate member 572 and a brush head 574. In some embodiments, the sample brush 570 is coupled to the cap 508. The sample brush 570 can be attached to the cap 508 by any means known in the art. The sample brush 570 can be integrally or monolithically formed with the cap 508. The sample brush 570 can be separate from the cap 508. The sample brush 570 may or may not be attached to the cap 508. The sample brush 570 can be detachable from the cap 508. The sample brush 570 can include perforations or score lines to facilitate detachment from the cap 508. The sample brush 570 can comprise a material including Nylon, any type of plastic, silicon, any artificial or natural materials, or combinations thereof. The sample brush 570 can be pre-infused with a solution including a mucolytic solution held within the transport tube 500.

FIG. 3A illustrates the transport tube 500 with the cap 508 attached. The sample brush 570 extends through the central hole 562. In some embodiments, the brush head 574 can extend past the screen 550. In some embodiments, the brush head 574 extends between the screen 550 and the cone 530 when the sample brush 570 is received within the transport tube 500. The brush head 574 can have a length to position the brush head 574 relative to the screen 550.

FIG. 3B illustrates the cap 508 removed from the elongate body 506. The sample brush 570 can be coupled to the cap 508 such that decoupling the cap 508 also decouples the sample brush 570. The elongate body 506 can include threads for engaging the cap 508. The screen 550 can be disposed within the elongate body 506. The cone 530 can be disposed within the elongate body 506. The screen 550 and the cone 530 can have a predetermined distance therebetween to accommodate the brush head 574, or a portion thereof. In some embodiments, the screen 550 and the cone 530 are fixed in position. In other embodiments, the screen 550 is axially movable. In some embodiments, the screen 550 is axially movable until the screen 550 abuts a stop within the elongate body 506, thereby preventing further movement of the screen 550 toward the cone 530.

The screen 550 can include fenestrations or pores 556. The pores 556 can be the same size. The pores 556 can be different sizes. The pores 556 can be evenly distributed along the conical portion 558. The pores 556 can be randomly distributed along the conical portion 558. In some embodiments, the cylindrical portion 554 does not include pores 556. The cylindrical portion 554 can be shaped to abut the elongate body 506. In some embodiments, the cylindrical portion 554 forms a seal with the inner surface of the tube. In some embodiments, the cylindrical portion 554 can have a wall thickness greater than the wall thickness of the conical portion 558. In other embodiments, the cylindrical portion 554 can have a wall thickness less than the wall thickness of the conical portion 558. In yet other embodiments, the cylindrical portion 554 can have a wall thickness equal to the wall thickness of the conical portion 558.

In some embodiments, the screen 550 can have a fenestration or pore size of between about 0.5 mm and about 7 mm, such as about 0.5 mm, 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, or more or less, or ranges including any two of the foregoing values. In some embodiments, a pore size of 4 mm best homogenizes the most viscous sample. In some embodiments, the pore size can be configured to take into account the viscosity of the biological sample.

FIGS. 3F-3J illustrate a transport tube 600 which can include any of the features of the devices, tubes, or containers described herein. The transport tube 600 can include a cap 608 with the cap 608 coupled in FIG. 3F and decoupled in FIG. 3G. The transport tube 600 can include a screen 650 having any feature of the screens described herein.

The transport tube 600 can include a top end 602 and a bottom end 604. The transport tube 600 can include wide-mouth top end 602 with a diameter greater than that of the bottom end 604. In some embodiments, the transport tube 600 can include a cone 630 which forms the bottom end. In other embodiments, the bottom end 604 is flat or generally flat. The transport tube 600 can include a frustoconical section 679 with a tapering diameter from top to bottom to transition zone 681. The transition zone 681 can have a narrower diameter, for example, cylindrical cross-section as shown. The transport tube 600 can include an upper section 694 which can be removably attachable and detachable to lower section 695. In the illustrated embodiment, the upper section 694 includes female threads and the lower section 695 includes male threads. The bottom end 604 can be coupled with a secondary cap 687. The transport tube 600 can be removably capped at both ends. In other embodiments, the bottom end 604 can be a closed end. In some embodiments, the secondary cap 687 is removably held at the bottom end 604. The bottom end 604 can be sealed by means other than the secondary cap 687. In some embodiments, the cone 630 forms the sealed bottom end. The secondary cap 687 can be coupled to the lower section 695 by any means described herein.

The secondary cap 687 can be attachable and/or detachable at an intermediate axial location along the transport tube 600. In some embodiments, the upper cap 608 can be removed, and the sample material can be funneled in through the top end 602, passing through narrowing diameter frustoconical/funnel section 679, past transition zone 681, and into elongate body 606 and optionally through screen 650. Once the sample moves in the lower section 695, the upper section 694 can be detached, for example by rotating the upper section 694 relative to the lower section 695. The secondary cap 687 or other cap can be secured to the lower section 695. The secondary cap 687 or other cap can be smaller diameter than the cap 608 for the wide-mouth detached open end 602. The secondary cap 687 or other cap forms a closure at the transition zone 681. The threads on the lower section 695 can couple to both the upper section 694 and any other closure device such as the secondary cap 687 or other cap. The transport tube 600 can include a brush (not shown). The brush can be separate from the secondary cap 687.

The lower section 695 can be an elongate body. The lower section 695 can be cylindrical in form, at least along the majority of the length of the lower section 695. The upper section 694 can include frustoconical/funnel section and tubular section. The transition point 681 between these two sections can be above the coupling mechanism between the upper section 694 and the lower section 695. The frustoconical/funnel section can have a larger diameter that tapers to a smaller diameter of the tubular section. The frustoconical/funnel section and tubular section can be integrally or monolithically formed of the same material. The frustoconical/funnel section and tubular section can be coupled together such as by adhesive, welding, friction fit, interference fit, detents, bonded, or any other means of coupling. In some embodiments, the open end diameter of the frustoconical/funnel section can be about, at least about, or no more than about 25%, 50%, 75%, 100%, 125%, 150%, 200%, of a diameter of the tubular section, or ranges including any two of the foregoing values. In some embodiments, the wide-mouth open end can have a diameter of 3 cm, 4 cm, 5 cm, 6 cm, 7 cm, 8 cm, 9 cm, 10 cm, or more or less, or ranges including any two of the foregoing values. In some embodiments, the tubular section can have a diameter of between about 0.5 cm, 1 cm, 1.5 cm, 2 cm, 2.5 cm, 3 cm, 3.5 cm, 4 cm, 4.5 cm, 5 cm, or more or less, or ranges including any two of the foregoing values.

Figure 3K:
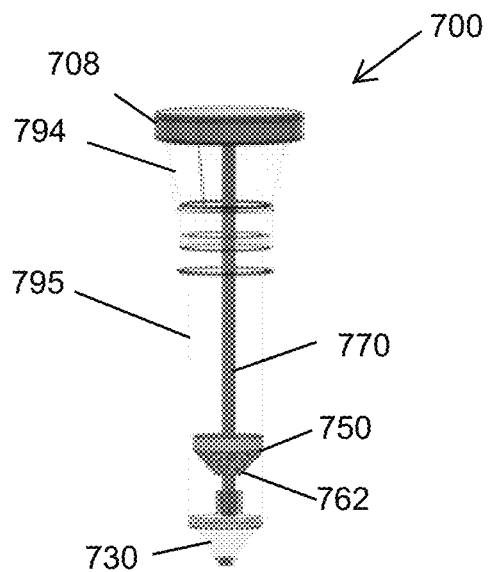
Figure 3L:
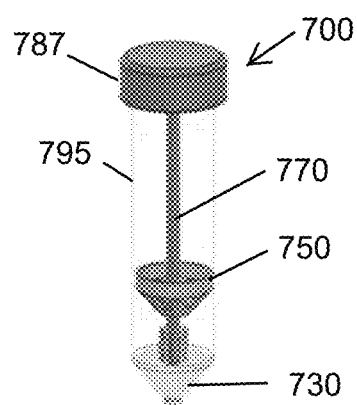

FIGS. 3K-3L illustrates a transport tube 700 which can include any of the features of the devices, tubes, or containers described herein. The transport tube 700 can include a cap 708 with the cap coupled to a sample brush 770. The transport tube 700 can include a screen 750 having any feature of the screens described herein. The sample brush 770 can extend from the cap 708 through a central hole 762 of the screen 750. The transport tube 700 can include a cone 730 which forms the bottom end of the tube. The transport tube 700 can include an upper section 794 and a lower section 795. In some embodiments, the upper section 794 can be removably attachable and detachable to the lower section 795. In some embodiments, the upper section 794 can be permanently affixed to the lower section 795. The upper section 794 can include a frustoconical/funnel section. The lower section 795 can include a tubular elongate section.

In some embodiments, the cone 730 is removably attachable and detachable to the lower section 795. The cone 730 can include male threads and the lower section 795 can include female threads. In some embodiments, the cone 730 can be permanently affixed to the lower section 795.

In some embodiments, the sample brush 770 is configured to be shortened. The sample brush 770 can include perforations or score lines to facilitate reducing the length of the sample brush 770. The sample brush 770 can be detached from the cap 708.

In some embodiments, the upper section 794 can be removed as described herein. The cap 708 can be removed. A secondary cap 787 can be coupled to the lower section 795 once the upper section 794 is removed. In some embodiments, the sample brush 770 is shortened and/or detached to fit within the shortened tube. The secondary cap 787 is at an intermediate axial location along the transport tube 700, at the top of the upper section 794.

Figure 4A:
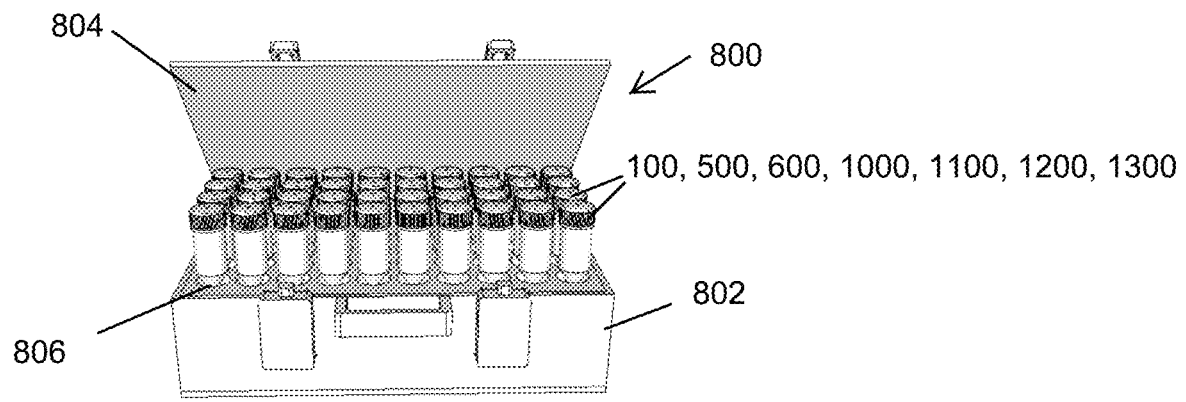
FIGS. 4A-4D illustrate embodiments of a storage and cooling system for sample collection tubes.
Figure 4B:
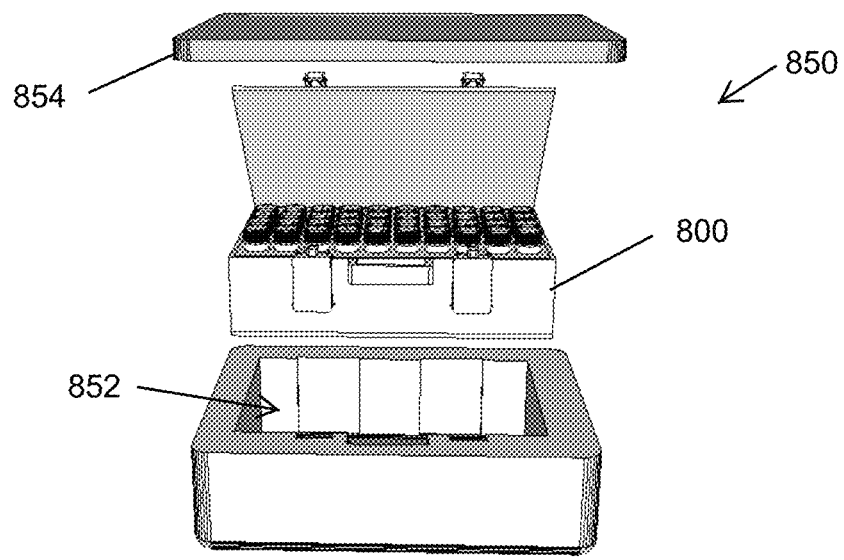
Figure 4C:
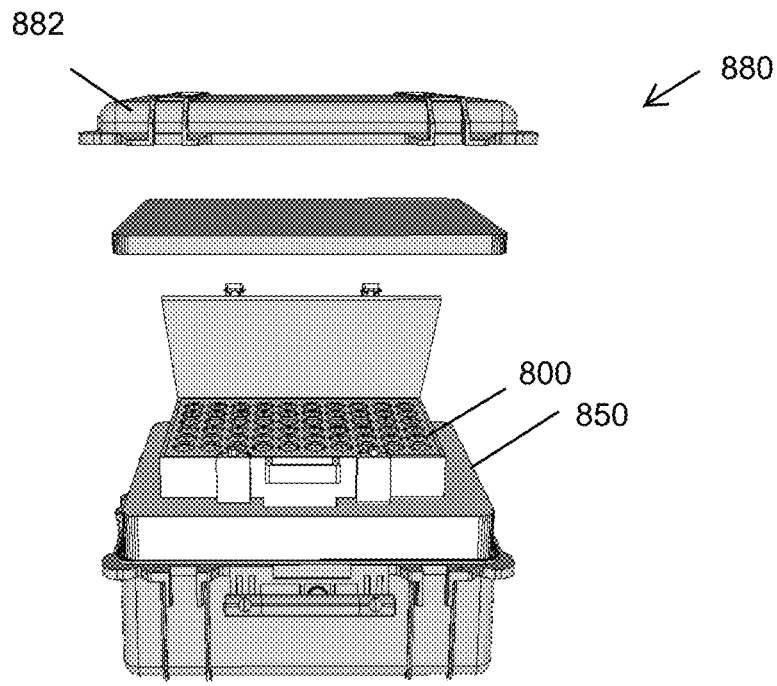
Figure 4D:
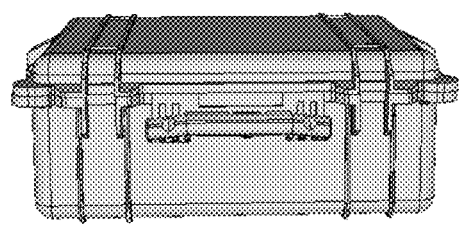

FIGS. 4A-4D illustrate embodiments of a storage and cooling system for sample collection tubes. FIG. 4A is a view of a storage case. FIG. 4B is an exploded view of a system including the storage case configured to fit in a cooling container. FIG. 4C is an exploded view of a system including the storage case and the cooling container configured to fit in a Pelican case. FIG. 4D illustrates a closed Pelican case. The storage case and the cooling container can be utilized independently of the Pelican case.

The system can include a storage case including a plurality of wells configured to hold transport tubes. The system can include a cooling container configured to sit in a Pelican case. The system can include customized dry ice or foam refrigerant elements surrounding the storage case to cool the samples. In some embodiments, the storage case can fit any number of transport tubes. In some embodiments, the storage case can fit all of the same type of transport tubes. In some embodiments, the storage case can fit different types of transport tubes.

FIG. 4A illustrates a storage case 800. The storage case 800 can include an outer shell 802, a movable lid 804, and an interior storage area with a plurality of wells 806 configured to fit sample containers, such as transport tubes including those disclosed herein.

FIG. 4B illustrates a cooling container 850. The storage case 800 can be configured to fit within a cavity 852, such as a large central cavity 852 of the cooling container 850. The cooling container 850 can include a lid 854 configured to enclose the cavity 852. The cavity 852 can be configured to accommodate dry ice, foam refrigerant pieces, or other cooling elements. These cooling elements can be placed around the storage case 800 within the cavity 852.

FIGS. 4C and 4D illustrate a Pelican case 880 or other enclosure. The storage case 800 within the cooling container 850 can be configured to be placed within the Pelican case 880. The Pelican case 880 can include a lid 882. In some embodiments, the storage case 800 can be utilized independently of the cooling container 850 and/or the Pelican case 880. In some embodiments, no cooling is required. In some embodiments, no transport is required.

In some embodiments, the storage, cooling, and transport system is designed for international/long distance collection and research. In some embodiments, the system can include a passive cooling system. The passive cooling system can include a custom-made dry ice, foam refrigerant pieces, or other cooling elements. In some embodiments, the system can include an active cooling system. The active cooling system can include a battery and a portable cooling unit integrated into the system. The active cooling system can include any mechanical cooling system, such as a fan, refrigerator, thermoelectric cooler or other active system.

The system can be customized to fit multiple transport tubes, devices, or containers. The system can be designed for domestic and international transport via shipping company or transport via personnel. The system can be designed to house a device to read the bar code, RFID chip, GPS, WiFi, Bluetooth, Bluetooth Low Energy (BLE), or any combination of the aforementioned. The system can be designed to be tracked. The system can be designed to track transport tubes. The system can track tubes based on labels on each transport tube. The transport tubes can be scanned by a reader and information can be gathered, stored, and retrieved to track the tubes. The system can be designed to house a device to track and transmit the location of the one or more transport tubes by means of a bar code, RFID chip, GPS, WiFi, Bluetooth, Bluetooth Low Energy (BLE), or any combination of the aforementioned, or by means of tracking.

Several examples below illustrate the advantageous early growth of a number of organisms on transport media including 50% glycerol, 20% Sputolysin® (Dithiothreitol), and 30% free water. Other media variations are also possible as disclosed, for example, elsewhere herein.

In some embodiments, an infectious organism transport media is provided. The infectious organism transport media can comprise at least about 50% glycerol. In some embodiments, the transport media can comprise at least about 65% glycerol. In some embodiments, the transport media can comprise at least about 80% glycerol. The infectious organism transport media can comprise at least about 5% of a mucolytic agent. In some embodiments, the transport media can comprise at least about 10% of a mucolytic agent. In some embodiments, the mucolytic agent comprises Sputolysin® (Dithiothreitol).

In some embodiments, the infectious organism transport media does not include any additional infectious organism growth agent. In some embodiments, the transport media can consist essentially of glycerol and mucolytic agent. In some embodiments, the transport media consists of glycerol and mucolytic agent.

Example 1

Figure 5A:
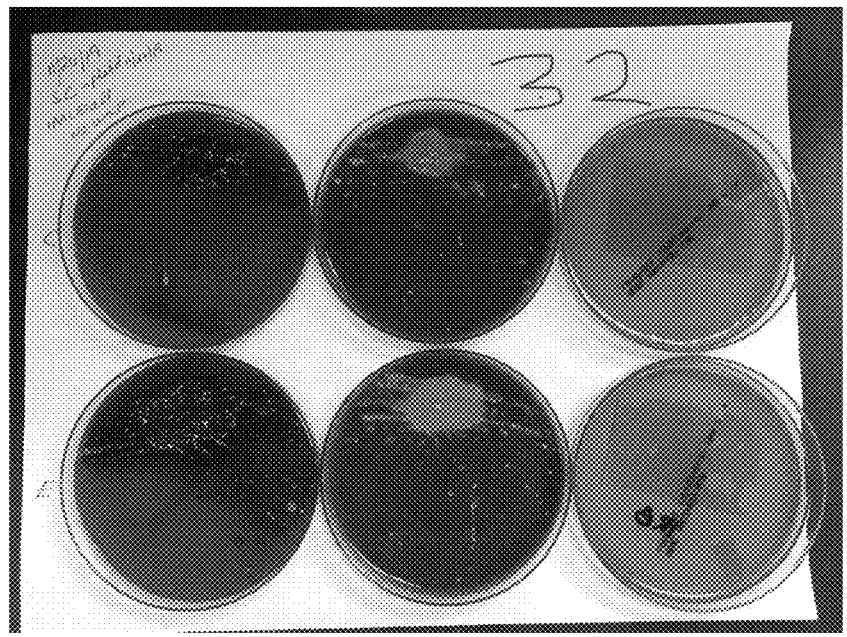
FIGS. 5A-5EE illustrate examples of culture processing results.

FIG. 5A illustrates *Streptococcus pneumoniae* isolated from experimental sample and not from control in sputum.

Figure 5B:
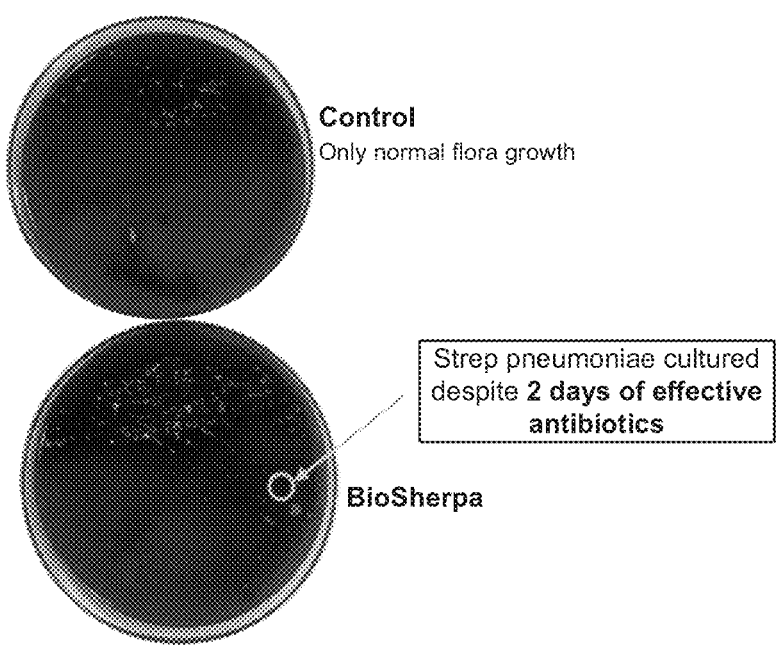

FIG. 5B illustrates control versus experimental results. The upper sample is a control with only normal flora growth. The bottom sample is utilizing the systems and methods described herein. The *Streptococcus pneumoniae* was cultured despite two days of effective antibiotics. There is one mucoid colony of alpha *Streptococcus* on the experimental sample not seen on control.

Figure 5C:
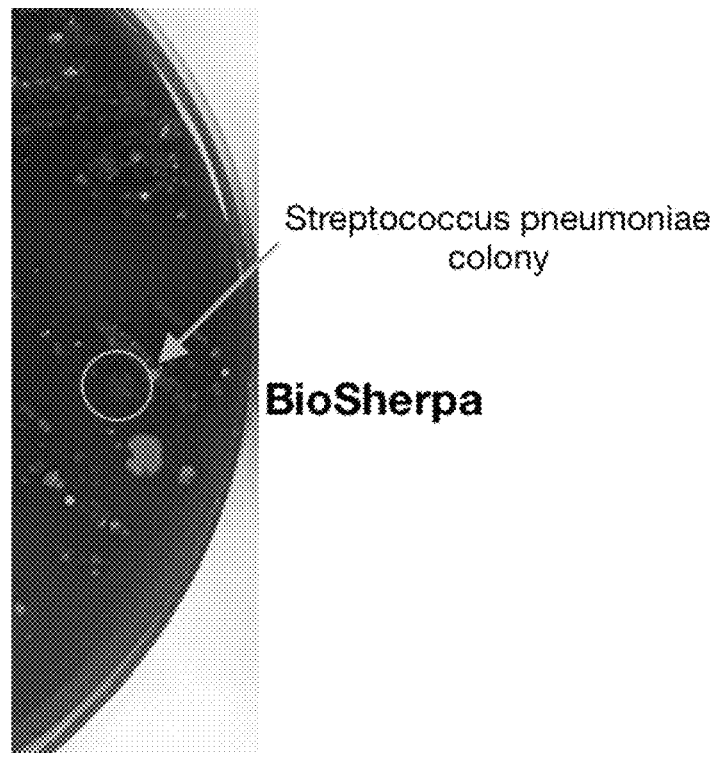

FIG. 5C illustrates an enlarged view of the *Streptococcus pneumoniae* colony.

Figure 5D:
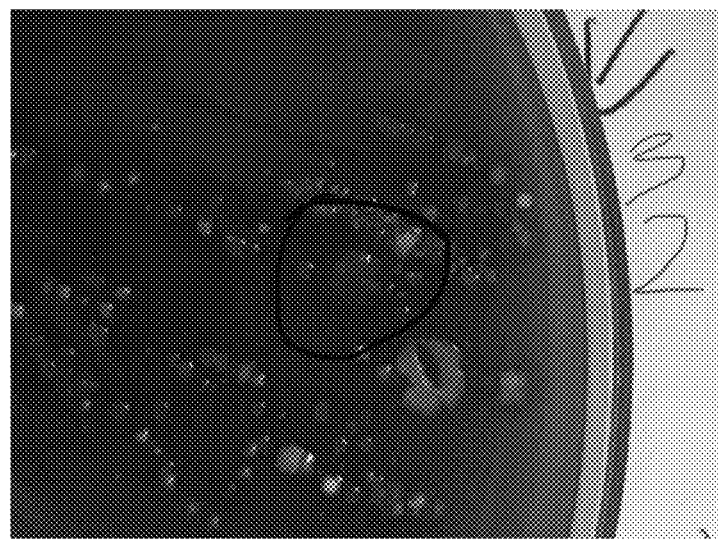

FIG. 5D illustrates another enlarged view of the *Streptococcus pneumoniae* colony. Further workup revealed *Streptococcus pneumonia*.

Figure 5E:
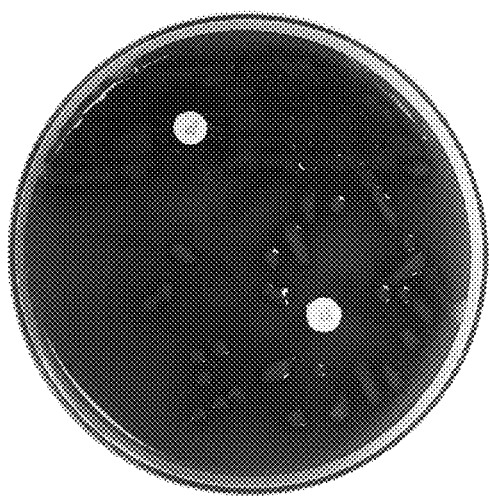

FIG. 5E illustrates the mucoid alpha *Streptococcus* only on the experimental sample is *Streptococcus pneumonia*. *Streptococcus pneumoniae* not isolated using standard methods. It has macrolide resistance indicating that it is resistant to commonly used macrolide drugs such as azithromycin.

The patient had invasive pneumococcal disease as noted by a positive *Streptococcus pneumoniae* urine antigen result. This sample is most impressive in that the systems and methods described herein allowed isolation of *Streptococcus pneumoniae* despite the patient being on ceftriaxone for two days at the time of collection. The isolate is sensitive to ceftriaxone according to the sensitivity pattern. S in the Interpretation column of the tables below indicates sensitivity, and R indicates resistance.

| 03 *S. Pneumoniae* | | |
| --- | --- | --- |
| Drug | MIC | Interpretation |
| Ceftriaxone | <=0.25 | S |
| Clindamycin | >0.5 | R |
| Erythromycin | >0.5 | R |
| Levofloxacin | 1 | S |
| Penicillin | <=0.03 | S |
| Vancomycin | 0.25 | S |

While not being bound to a specific theory, the use of the systems and methods described herein may have facilitated breakdown of the protective biofilm in the sputum sample and release of the sessile bacterium into media creating a culturable planktonic organism. The biofilm likely protected the isolate from ceftriaxone while in vivo.

The systems and methods described herein allowed for streamlined antibiotic therapy and conferred epidemiologically important data indicating that macrolide resistance is present in our patient population.

Example 2

Figure 5F:
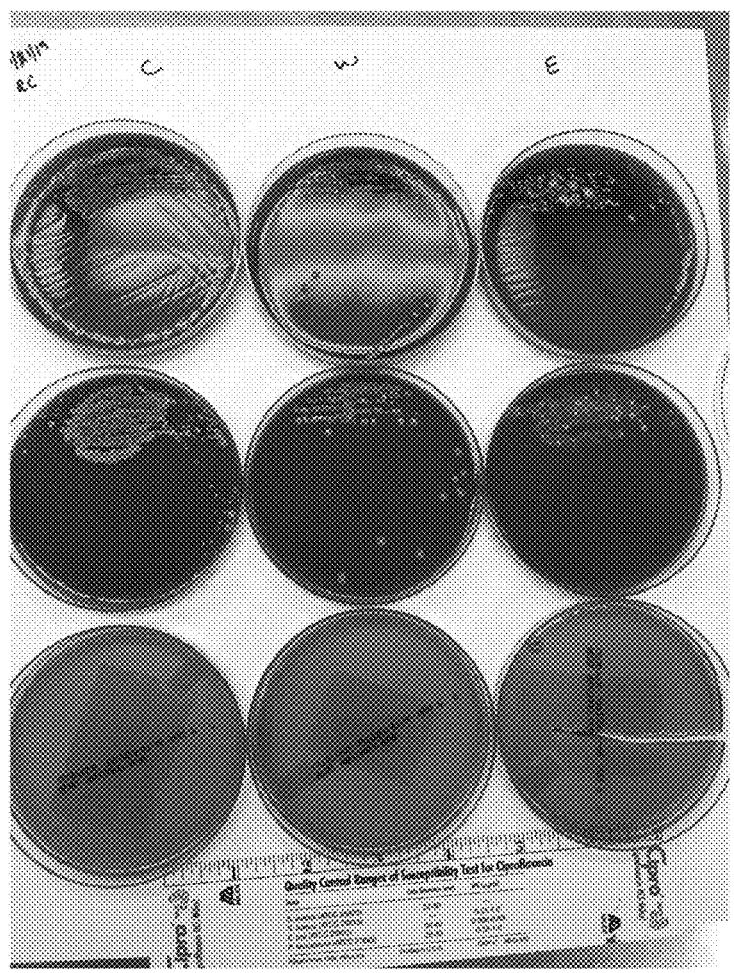

FIG. 5F illustrates *Klebsiella oxytoca* isolated from experimental sample and not from control in sputum. The systems and methods described herein facilitated growth of *Klebsiella oxytoca* from the experimental sample that was not present on control samples.

Figure 5G:
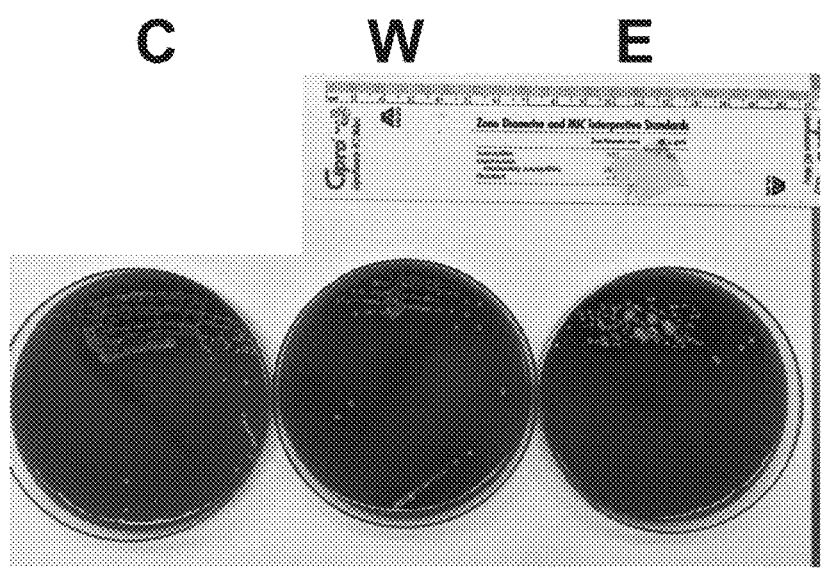

FIG. 5G illustrates the cultures. *Klebsiella* was not isolated using either standard streaking techniques or the WASP automatic plating technique. It is most prevalent on the blood agar and the MacConkey agar.

Figure 5H:
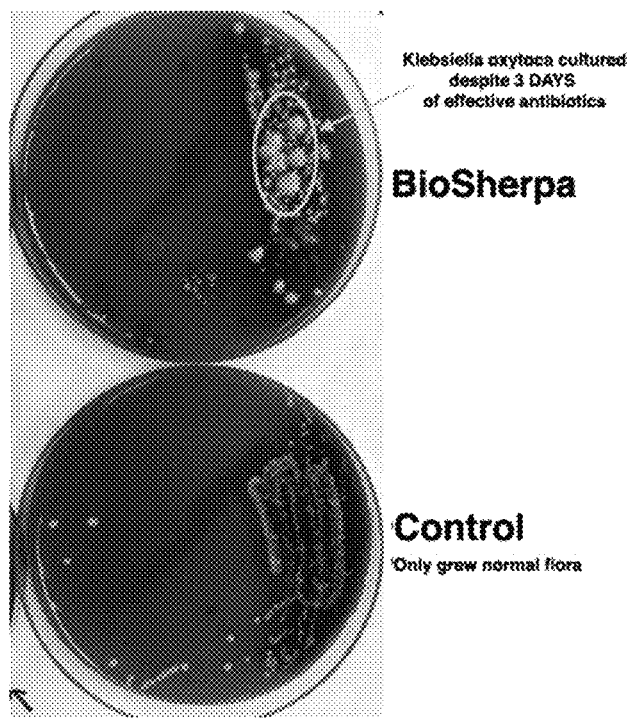

FIG. 5H illustrates *Klebsiella oxytoca* cultured despite three days of effective antibiotics. The top plate shows the use of systems and methods described herein. The bottom control only grew normal flora.

Figure 5I:
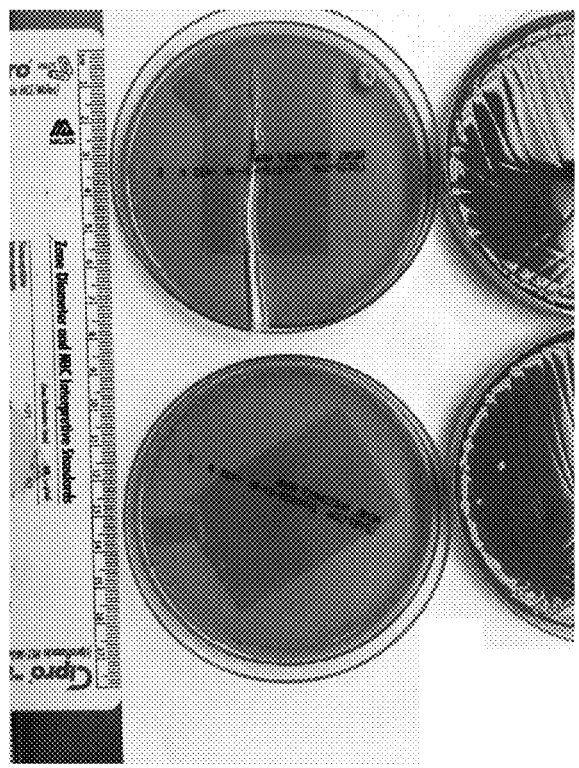

FIG. 5I illustrates the cultures. This patient was also on active antibiotic therapy at the time of collection. Despite three days of ceftriaxone, the systems and methods described herein facilitated the isolation of the organism. The organism is sensitive to ceftriaxone.

| 01 *Klebsiella oxytoca* | | |
| --- | --- | --- |
| Drug | MIC | Interps |
| Amikacin | <=16 | S |
| Amox/K Clav | <=4/2 | S |
| Amp/Sulbactam | 8/4 | S |
| Ampicillin | >16 | R |
| Cefazolin | 8 | R |
| Cefepime | <=2 | S |
| Cefotaxime | <=2 | S |
| Cefoxitin | <=8 | S |
| Ceftriaxone | <=1 | S |
| Ciprofloxacin | <=1 | S |
| Gentamicin | <=1 | S |
| Imipenem | <=0.5 | S |
| Levofloxacin | <=0.25 | S |
| Meropenem | <=1 | S |
| Tetracycline | <=4 | S |
| Tobramycin | <=1 | S |
| Trimeth/Sulfa | <=2/38 | S |

While not being bound to a specific theory, the organism may have been shielded from antibiotic effect in a native biofilm environment in vivo. These results again allowed us to decrease antibiotic exposure by eliminating broad spectrum therapy.

Example 3

Figure 5J:
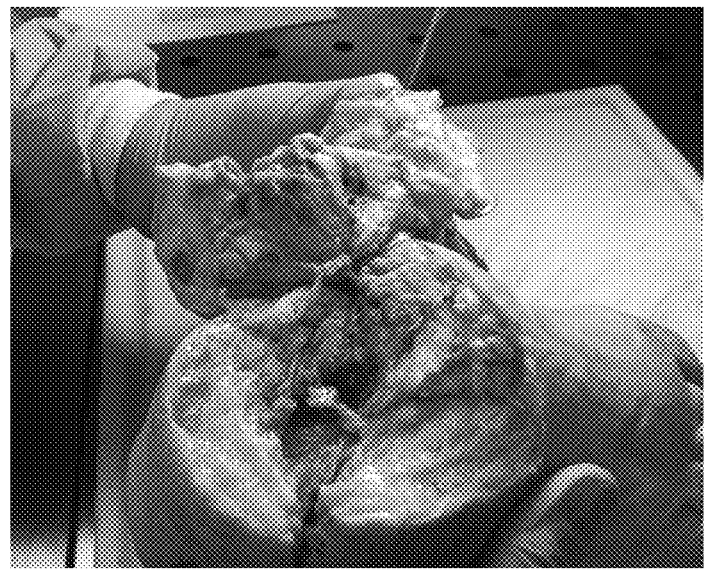

FIG. 5J shows a patient that suffered from a hematogenous osteomyelitis in the right ankle. The patient was treated with multiple weeks of intravenous and oral antibiotics. The ankle never completely healed ultimately requiring amputation. This example relates to incubation in the systems described herein yields growth of indolent *S. aureus* infection.

Figure 5K:
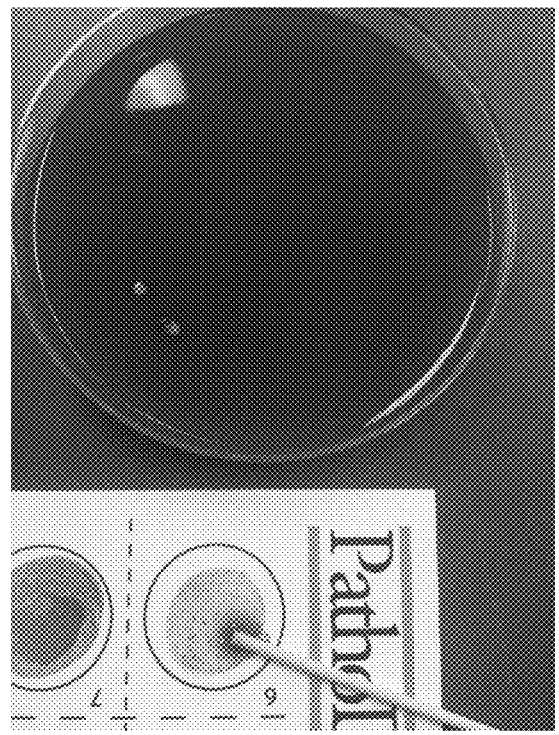

FIG. 5K illustrates a view of the cultures using systems and methods described herein.

Figure 5L:

FIG. 5L illustrates another view of the cultures. The cultures of the bone taken after amputation were negative. However, after the bone was incubated in the systems described herein there was growth. The sample was incubated for 24 hours at 37 degrees Celsius. This figure illustrates obvious growth of *S. aureus*.

While not being bound to a specific theory, the native bone may sequester sessile infection in biofilms, especially in relatively devitalized bone associated with vasculopathy. Incubation in mucolytic allows for breakdown of the biofilm and the glycerol broth allows for a nutritive environment to coax these recalcitrant organisms into a cultivable state. The organism isolated is the same as that in the original blood culture as shown below.

| Original Blood Culture Rare Colonies *Staphylococcus aureus* | | |
| --- | --- | --- |
| Drug | MIC | Interps |
| Amp/Sulbactam | <=8/4 | S |
| Cefazolin | <=4 | S |
| Clindamycin | <=0.25 | S |
| Daptomycin | 0.5 | S |
| Gentamicin | <=1 | S |
| Linezolid | 2 | S |
| Oxacillin | <=0.25 | S |
| Rifampin | <=1 | S |
| Tetracycline | >8 | R |
| Trimethoprim/Sulfa | <=0.5 | S |
| Vancomycin | 1 | S |

| O5 S. aureus | | |
|---|---|---|
| Drug | MIC | Interps |
| Amp/Sulbactam | <=8/4 | S |
| Cefazolin | <=4 | S |
| Clindamycin | <=0.25 | S |
| Daptomycin | 0.5 | S |
| Gentamicin | <=1 | S |
| Linezolid | 2 | S |
| Oxacillin | <=0.25 | S |
| Rifampin | <=1 | S |
| Tetracycline | >8 | R |
| Trimethoprim/Sulfa | <=0.5 | S |
| Vancomycin | 1 | S |

This result has clinical relevance. This result indicates that longer antibiotic therapy and/or the use of a biofilm active agent such as rifampin may be necessary in some cases of osteomyelitis.

Example 4

Figure 5M:
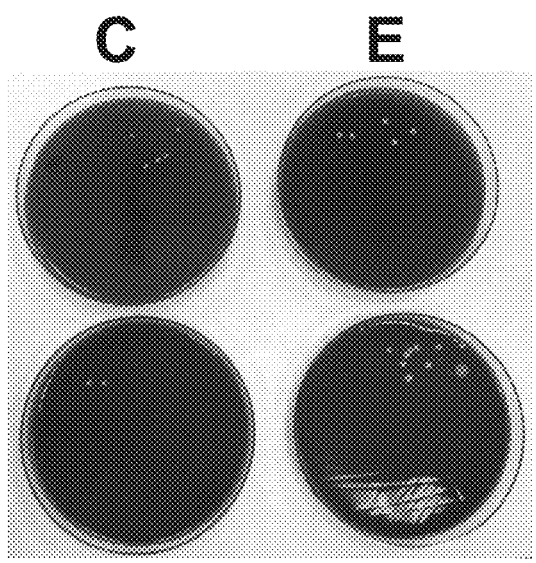

FIG. 5M illustrates the use of systems and methods to isolate MRSA in sputum allowing for faster initiation of anti-MRSA therapy and clinical cure. This patient was intubated for hypoxemia and pneumonia. The patient placed on ceftriaxone and azithromycin. The systems and methods allowed identification of MRSA in the patient's sputum.

Figure 5N:
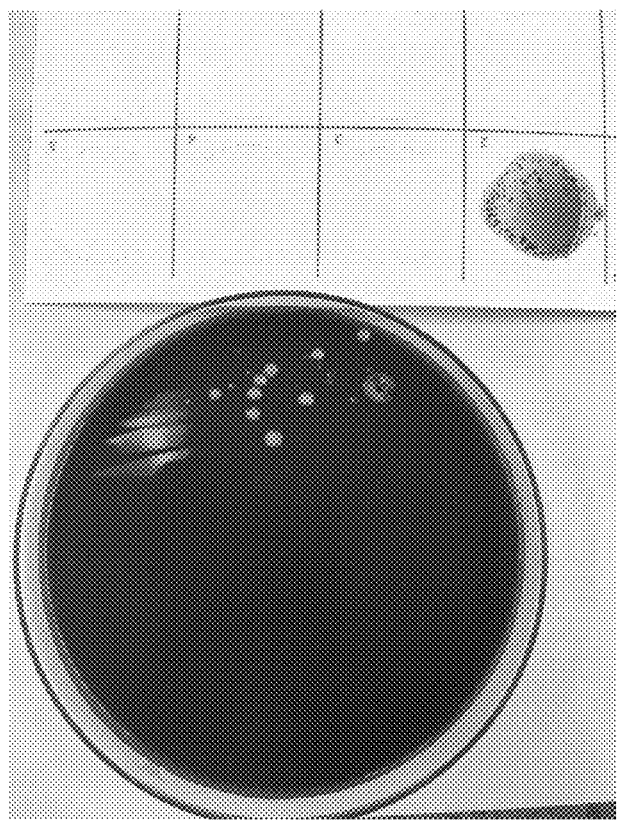

FIG. 5N illustrates the yellow colony in the experimental site is obvious. The patient decompensated clinically to the point of near death until proper MRSA antibiotic therapy was initiated. Hypoxemia worsened and oxygen requirements increased prior to MRSA therapy.

| Vital Signs | | |
|---|---|---|
| Label | Value | Date Time |
| Bedside Pulse Oximetry | 89% L | May 7, 2020 1349 |
| Bedside Pulse Oximetry | 95% | May 7, 2020 0741 |
| Bedside Pulse Oximetry | 94% | May 7, 2020 0417 |
| Bedside Pulse Oximetry | 93% | May 7, 2020 0010 |
| Bedside Pulse Oximetry | 94% | May 6, 2020 2000 |
| Bedside Pulse Oximetry | 96% | May 6, 2020 1515 |

| Item | Value | Date Time |
|---|---|---|
| Oxygen Flow Rate | 30.0 L/min | May 7, 2020 1349 |
| Oxygen Delivery Method | Bi/PAP | May 7, 2020 1349 |
| Oxygen Delivery Method | Non-Rebreather | May 7, 2020 1000 |
| Oxygen Delivery Method | Nasal Cannula | May 7, 2020 0741 |
| Oxygen Delivery Method | Nasal Cannula | May 7, 2020 0417 |
| Oxygen Flow Rate | 2.0 L/min | May 7, 2020 0417 |
| Oxygen Delivery Method | Nasal Cannula | May 7, 2020 0010 |
| Oxygen Delivery Method | Nasal Cannula | May 6, 2020 2000 |
| Oxygen Delivery Method | Nasal Cannula | May 6, 2020 2000 |
| Oxygen Delivery Method | Nasal Cannula | May 6, 2020 1515 |

Linezolid/vancomycin therapy allowed the patient to come off the ventilator and the patient was ultimately discharged from the hospital.

The original culture taken on 5/5 (finalized on 5/7) was identical to a subsequent culture taken on 5/14 that only grew MRSA.

| S. aureus 5/14 Sputum cx | | |
|---|---|---|
| Drug | MIC | Interps |
| Amp/Sulbactam | <=8/4 | R |
| Cefazolin | 16 | R |
| Clindamycin | >4 | R |
| Gentamicin | <=1 | S |
| Linezolid | 2 | S |
| Oxacillin | >2 | R |
| Rifampin | <=1 | S |
| Tetracycline | <=1 | S |
| Trimethoprim/Sulfa | <=0.5 | S |
| Vancomycin | 2 | S |

| 5/5 Sputum cx Positive for MRSA | | |
|---|---|---|
| Drug | MIC | Interps |
| Amp/Sulbactam | <=8/4 | R |
| Cefazolin | 8 | R |
| Clindamycin | >4 | R |
| Gentamicin | <=1 | S |
| Linezolid | 2 | S |
| Oxacillin | >2 | R |
| Rifampin | <=1 | S |
| Tetracycline | <=1 | S |
| Trimethoprim/Sulfa | <=0.5 | S |
| Vancomycin | 2 | S |

While not being bound to a specific theory, early therapy with ceftriaxone and azithromycin may have treated some of the patient's pneumonia, hence the patient's initial improvement, but ultimately allowed the MRSA that was colonizing the patient's airway to infect tissue and cause a nosocomial infection. The systems and methods described herein allowed recognition of the presence of the pathogen early, allowing a change in therapy in a timely fashion, and ultimately save the patient's life.

Example 5

Figure 5O:
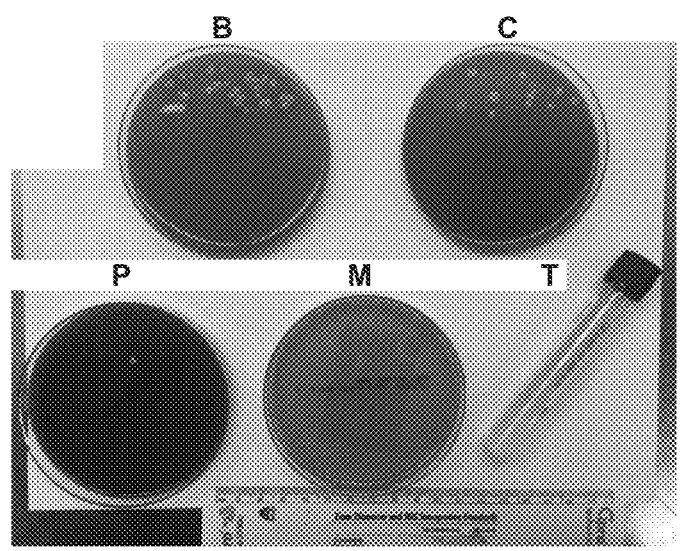

FIG. 5O illustrates the systems and methods described herein grew multiple additional pathogens from a bone sample while on broad spectrum antibiotics. This patient underwent transmetatarsal amputation for a severe skin/soft tissue infection despite treatment with broad-spectrum antibiotic therapy, vancomycin and piperacillin/tazobactam, for six days. The treated bone sample using systems and methods described herein grew S. aureus, S. epidermidis, Rothia mucilaginosa, S. warneri and H. parainfluenzae.

Figure 5P:
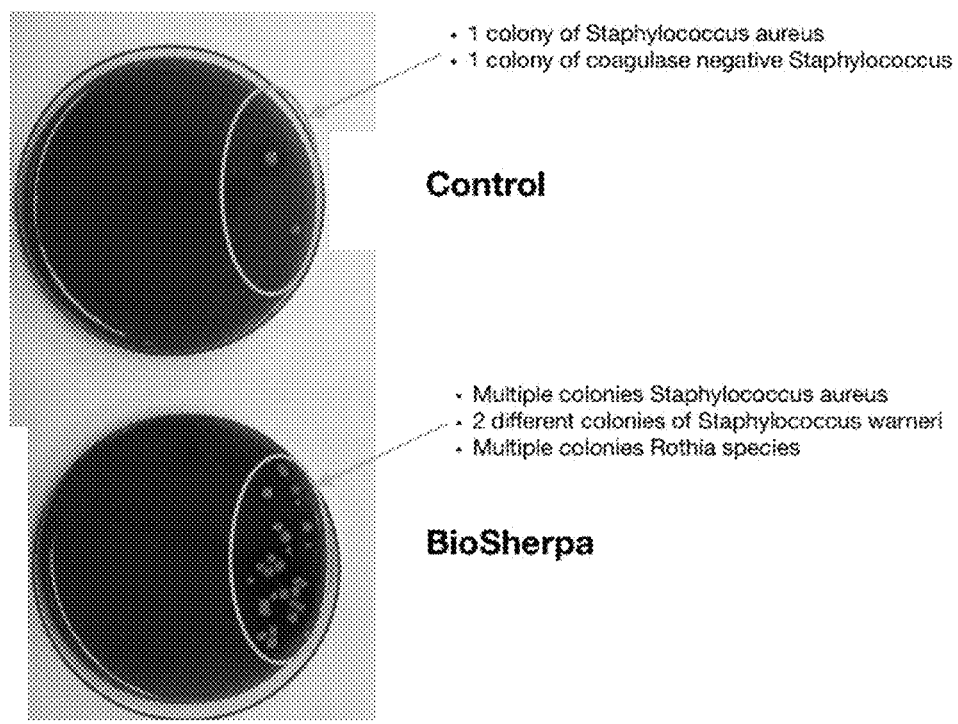

FIG. 5P illustrates the control that includes one colony of Staphylococcus aureus and one colony of coagulase negative Staphylococcus. The sample using the systems and methods described herein has multiple colonies of Staphylococcus aureus, two different colonies of Staphylococcus warneri, and multiple colonies of Rothia species.

Figure 5Q:
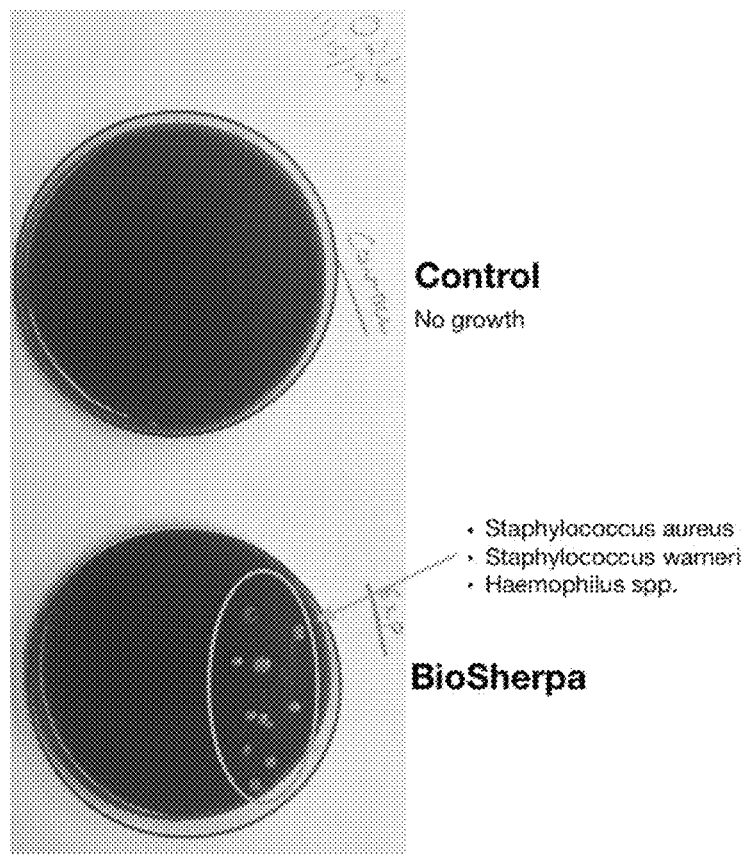

FIG. 5Q illustrates the control with no growth. The sample using the systems and methods described herein has Staphylococcus aureus, Staphylococcus warneri, and Haemophilus species.

Figure 5R:
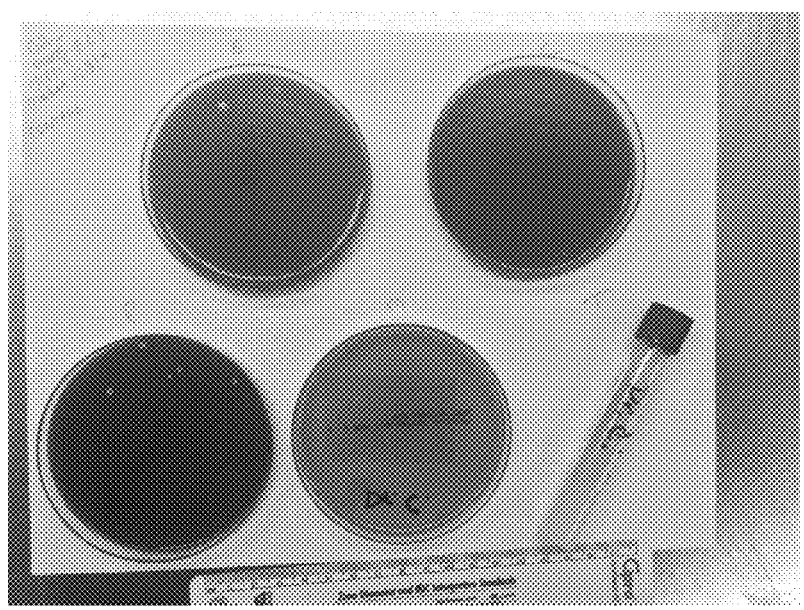

FIG. 5R illustrates that the standard sample only grew S. aureus and S epidermidis.

The systems and methods described herein facilitated growth of multiple organisms from a surgical biopsy culture. While not being bound to a specific theory, the organisms were shielded in biofilm in native but devitalized bone and were coaxed into cultivable states by the media.

Example 6

Figure 5S:
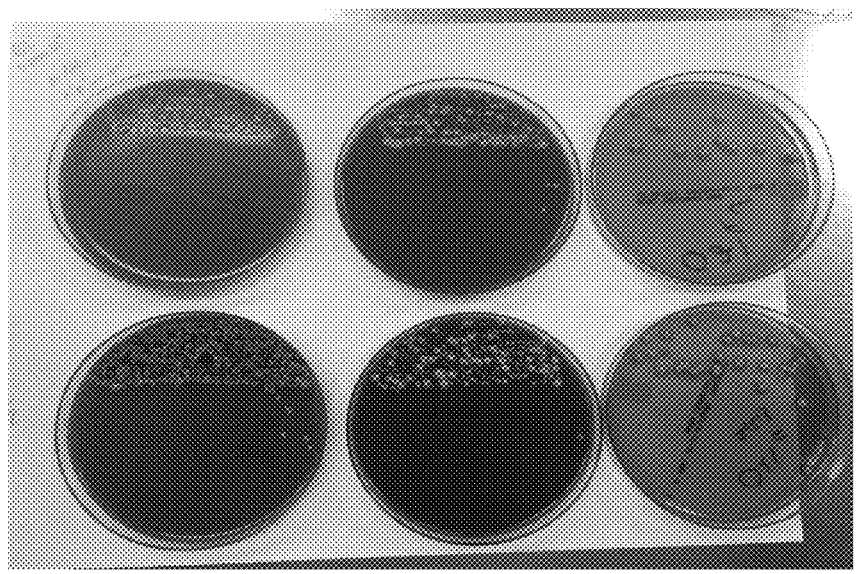

FIG. 5S illustrates the systems and methods described herein allowed sputum sample to be frozen and reanimated and showed additional pathogens. A sputum sample showed growth of *Klebsiella* in control and experimental samples. More organisms were isolated on the treated sample using the systems and methods described herein.

Figure 5T:

FIG. 5T illustrates the results when the same sample was frozen and reanimated after several days. The *Klebsiella* was again isolated and *S. aureus* was isolated as well. It is the beta-hemolytic colony on the blood plate.

Treatment using systems and methods described herein allowed abundant growth despite freezing. While not being bound to a specific theory, the glycerol component is cytoprotective. The extra time in the media allowed the release of *S. aureus* from biofilm and it was isolated as well.

This can have substantial clinical utility. Samples can be frozen for long duration storage and reanimated. It is beneficial to store intact samples versus only the bacteria isolated. For example, one can envision a need to measure cytokine concentrations in COVID-19 patients where "cytokine storm" appears to be part of the pathological process. Systems and methods described herein also allows for the original sample to be frozen, as opposed to isolated bacteria alone and freezing, so that other components of sputum such as lung parenchymal cells and cytokines can be measured.

Example 7

Figure 5U:
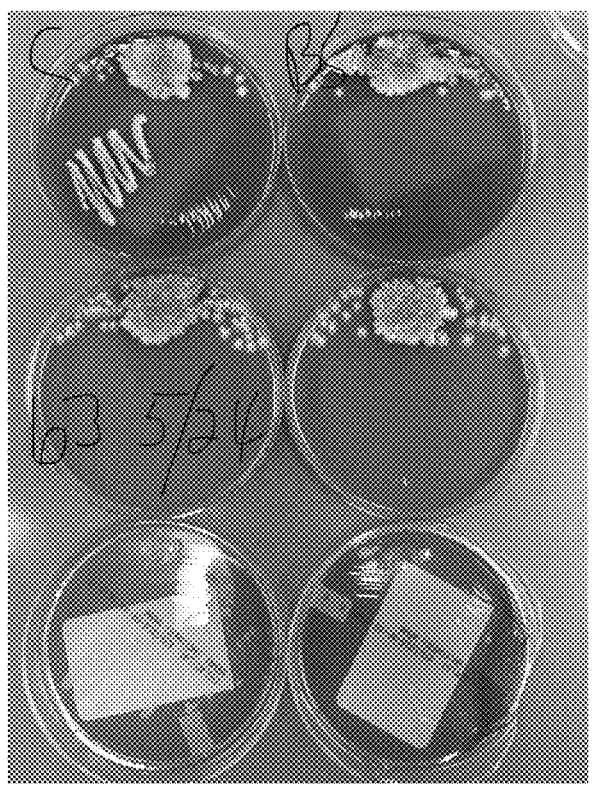

FIG. 5U illustrates the systems and methods described herein allowed sputum sample to be refrigerated and reanimated with no loss of pathogen. *Serratia* was isolated in control and experimental samples.

Figure 5V:
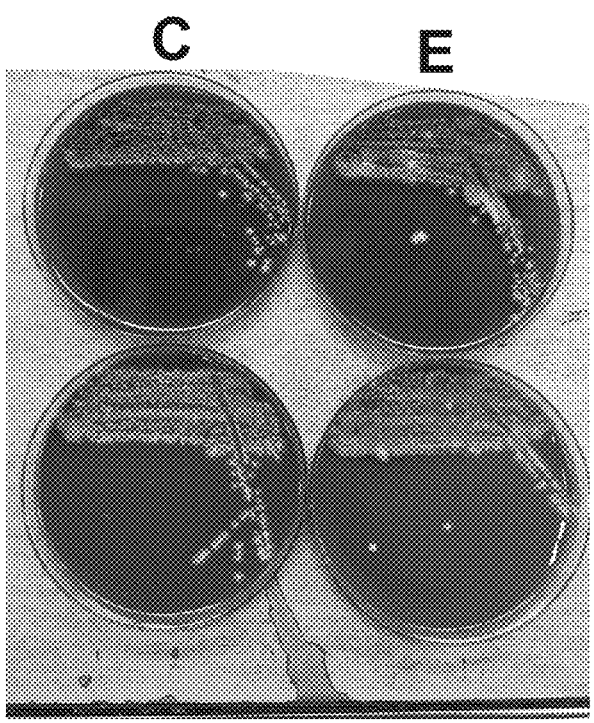

FIG. 5V illustrates when the control and treated samples using the systems and methods described herein were refrigerated for 48 hours and recultured, the treated samples showed significantly better growth of the *Serratia*.

Figure 5W:
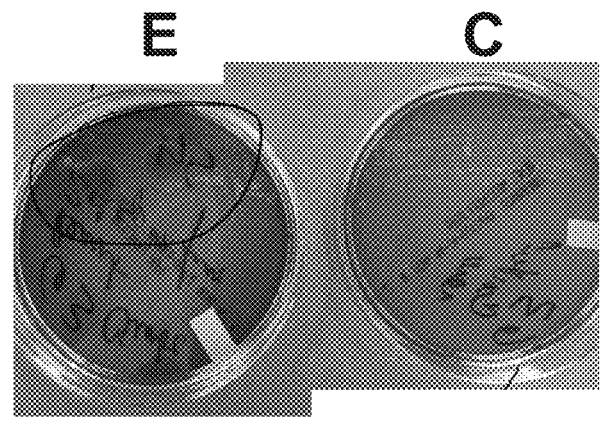

FIG. 5W illustrates growth after 48 hours of refrigeration. The *Serratia* was isolated on blood, chocolate and MacConkey agar from the treated sample using systems and methods described herein but only weakly on chocolate on the control sample.

The system and methods described herein continues the breakdown of natural biofilms and allows bacteria to be nourished even in refrigerated samples allowing for the transport of samples over long distances with no loss of pathogen viability.

While not being bound to a specific theory, this may mitigate the deterioration of pathogen viability during the common practice of transporting samples to centrally-located microbiology labs over the course of hours to days.

Example 8

Figure 5X:
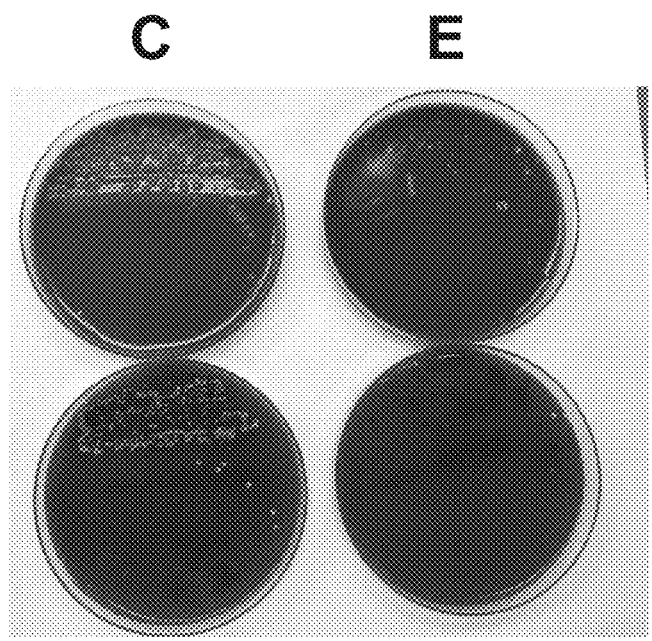

FIG. 5X illustrates systems and methods described herein support the growth and culture of nutritionally variant Streptococci in sputum. Nutritionally variant Streptococci are notoriously difficult to culture using standard techniques. Despite being a proven cause of human disease, they are often missed or do not grow in standard cultures. The systems and methods described herein offer a growth advantage to these organisms. *S. dysgalactiae* was isolated in sputum samples treated with transport media using systems and methods described herein. Control samples grew none.

Figure 5Y:
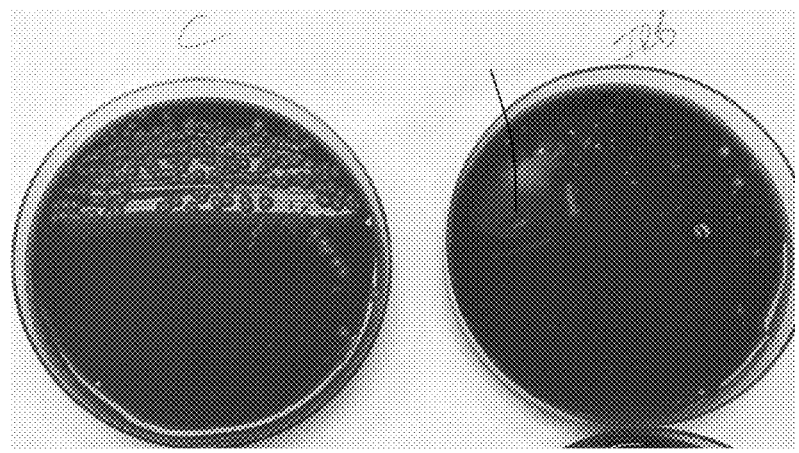

FIG. 5Y illustrates an enlarged view.

Figure 5Z:
Figure 5A:
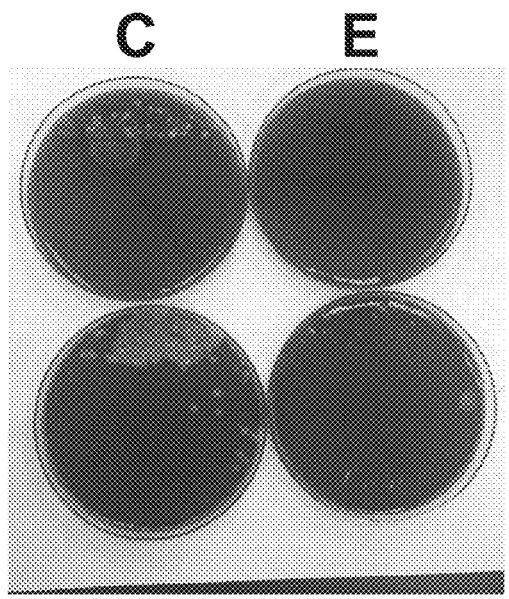
Figure 5B:
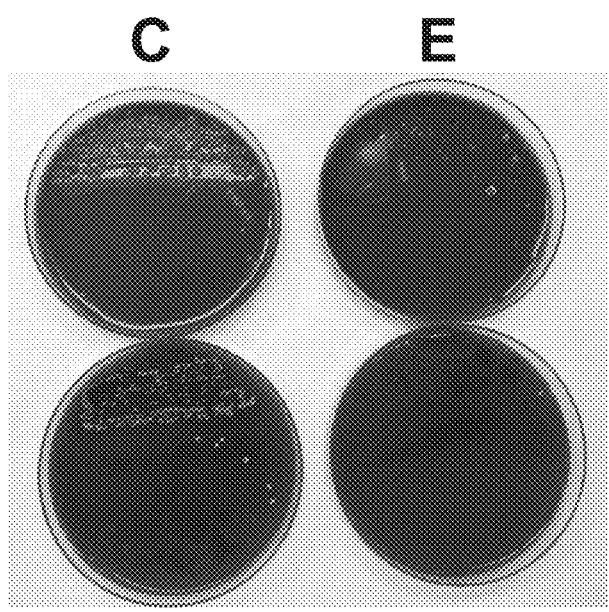
Figure 5C:
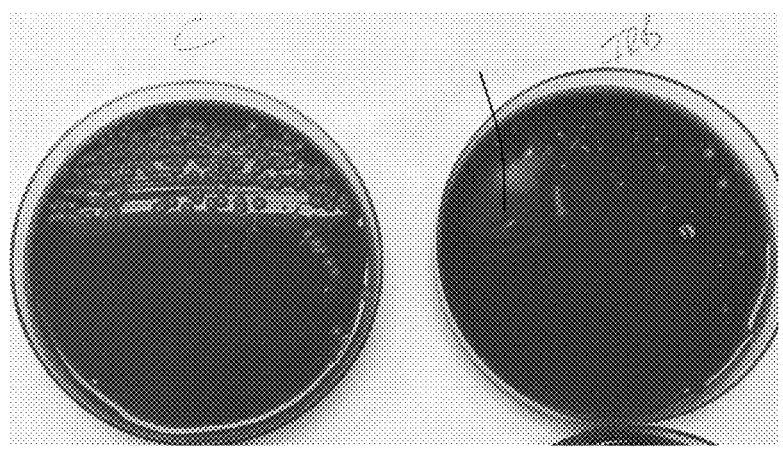
Figure 5D:
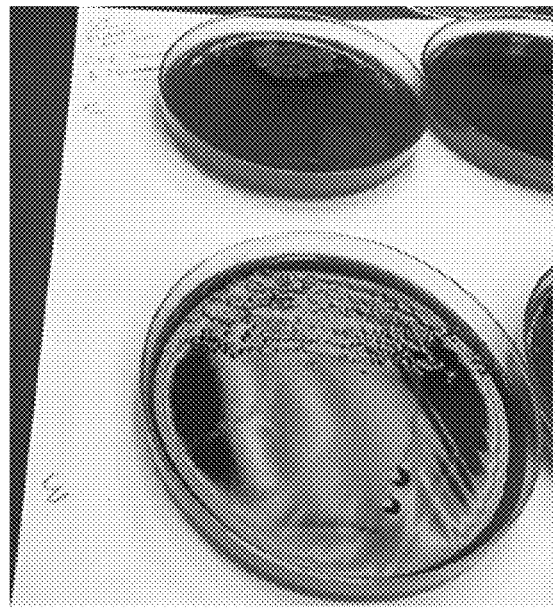
Figure 5E:
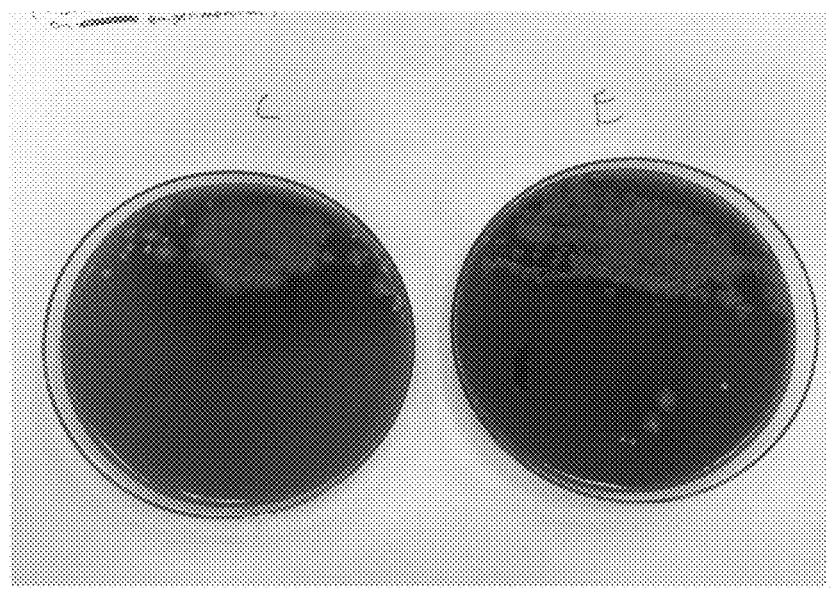

FIG. 5Z illustrates an enlarged view of Granulicatella species isolated using the method. It is another type of nutritionally variant streptococci.

FIG. 5AA illustrates Granulicatella spp was isolated in sputum samples treated with transport media using systems and methods described herein. Control samples grew none.

Clinically, the identification of these organisms is relevant as they often have distinct antibiotic resistance patterns (e.g. beta-lactam resistance).

Example 9

FIG. 5BB illustrates that systems and methods described herein attenuates yeast overgrowth allowing for easier detection of pathogens. This sample was treated using system and methods described herein.

FIG. 5CC illustrates an enlarged view. Yeast growth is attenuated but not fully suppressed. Pathogens are more easily isolated. There is precedence for partial suppression of yeast growth in culture by glycerol.

Yeast is rarely if ever a pulmonary pathogen. It is frequently an oral commensal organism. It tends to overgrow sputum samples if culture is delayed after the sample is obtained. While not being bound to a specific theory, the systems and methods described herein have no known effect on the growth of mold which can be a true pulmonary pathogen. In addition, the growth of the yeast is not fully suppressed, allowing the documentation of its presence if needed.

Example 10

FIG. 5DD illustrates 24 hours of growth on a glycerol-based transport media without any additional infectious organism growth agents. The "swarming" characteristic of the *Proteus* is evident on the experimental plate (E-bottom). It is easily distinguishable from the *Pseudomonas* also growing on both plates. There is no clear growth of *Proteus* on the control plate (C-top).

FIG. 5EE illustrates 48 hours of incubation. The experimental plate (E-right) is covered with *Proteus* to the point that the plate no longer looks like a blood plate while the control plate (C-left) is just starting to show growth of *Proteus* at this point.

This experiment illustrates the systems and methods described herein support faster growth of pathogens. *Proteus* was isolated a full 24 hours earlier allowing for clinical modification of the patient's care. The patient desaturated on Day 2 as shown in the table below. This is the same day the *Proteus* was recognized on the experimental plate.

| Date Time | Temp (F) | Pulse | Resp Rate | BP (MAP) | $O_2$ Sat | $O_2$ Delivery |
|---|---|---|---|---|---|---|
| Day 2 11:06 | | | | 117/67 | | |
| Day 2 06:44 | | | | | 92 | Non-Rebreather |
| Day 2 06:43 | | | 22 | | | |
| Day 2 06:43 | | 90 | 22 | | | |
| Day 2 06:00 | | | | | 84 | Non-Rebreather |

-continued

| Date Time | Temp (F) | Pulse | Resp Rate | BP (MAP) | O₂ Sat | O₂ Delivery |
|---|---|---|---|---|---|---|
| Day 2 04:00 | | | | | | Nasal Cannula |
| Day 2 04:00 | 97.9 | 78 | 21 | 123/58 (79) | 95 | Nasal Cannula |
| Day 2 00:00 | 98.1 | 89 | 18 | 115/60 (78) | 93 | Nasal Cannula |
| Day 2 00:00 | | | | | | Nasal Cannula |
| Day 1 22:39 | | | | 97/66 | | |
| Day 1 20:16 | | | | 107/69 | | |
| Day 1 20:00 | | | | | | Nasal Cannula |
| Day 1 20:00 | 97.5 | 93 | 18 | 107/63 (78) | 91 | Nasal Cannula |
| Day 1 16:49 | 97.0 | 87 | 24 | 93/61 (72) | | |
| Day 1 16:00 | | | | | | Nasal Cannula |

Antibiotics were expanded that morning. Initiation of a new antibiotic (made possible by recognizing the pathogen 24 hours earlier) lead to clinical improvement as evidenced by the patient's white blood count returning to close to normal range within 48 hours after the antibiotic change, and to within normal range within 72 hours after the antibiotic change.

| Date | White Blood Count (4-11 normal range) |
|---|---|
| Day 1 | 17.8 |
| Day 2 | 18.2 |
| Day 3 | 17.6 (antibiotic change) |
| Day 4 | 15.5 |
| Day 5 | 11.6 |
| Day 6 | 8.9 |

In some embodiments, a method of collecting organisms on transport media is provided. The method can comprise contacting a biological sample with sample transport media. The transport media can be any transport media described herein. The transport media can comprise at least about 50% glycerol. The transport media can comprise at least about 5% of a mucolytic agent. The infectious organism transport media does not include any additional infectious organism growth agent, in some embodiments. The method can comprise sending the sample to a laboratory for culturing. Contacting the biological sample can comprise placing the biological sample in a transport tube comprising the sample transport media, a screen, and a sampling brush.

In some embodiments, a method of culturing organisms on transport media is provided. The method can comprise receiving a biological sample associated with transport media. The transport media can be any transport media described herein. The transport media can comprise at least about 50% glycerol. The transport media can comprise at least about 5% of a mucolytic agent. The infectious organism transport media does not include any additional infectious organism growth agent, in some embodiments. The method can comprise incubating the biological sample to culture one or more organisms.

The method can comprise identifying the one or more cultured organisms. The cultured organisms can comprise bacterial organisms. The cultured organisms comprise viral organisms. The cultured organisms comprise fungal organisms. The cultured organisms comprise parasitic organisms. The one or more cultured organisms is selected from the group consisting of: Haemophilus influenzae, Klebsiella pneumoniae, Acinetobacter baumannii, Pseudomonas aeruginosa, Stenotrophomonas maltophilia, Streptococcus pneumonia, Moraxella catarrhalis, Serratia marcescens, Pasteurella multocida, Group G streptococcus, Citrobacter freundii, Enterobacter aerogenes, Proteus mirabilis, extended-spectrum beta-lactamase producing Enterobacteraciae, methicillin-resistant Staphylococcus aureus, multi-drug resistant Streptococcus pneumoniae, Helicobacter pylori, Mycobacterium tuberculosis, Mycobacterium avium-intracellulare, other mycobacterium, and vancomycin-resistant Enterococcus. The cultured organisms can be identified within about 36 hours after incubation or after sample collection. The cultured organisms can be identified within about 24 hours after incubation or after sample collection. The method can comprise freezing and thawing the biological sample, wherein the biological sample is frozen and thawed while preserving cellular wall integrity. The method can comprise incubating the sample at a desired temperature for up to 24 hours in order to increase the density of bacteria in samples with low initial bacterial density at collection. The desired temperature can be about 37° C. The method can comprise performing antimicrobial sensitivity studies on the cultured organisms.

In some embodiments, a biological transport system is provided. The biological transport system comprises any number of features disclosed herein. In some embodiments, a method of culturing organisms on transport media is provided. The method comprises any number of features as disclosed herein.

The following example embodiments with reference to clauses identify some possible permutations of combinations of features disclosed herein, although other permutations of combinations of features are also possible including those described in the claims.

Clause 1. An infectious organism transport media, comprising: at least about 50% glycerol, and at least about 5% of a mucolytic agent, wherein the infectious organism transport media does not include any additional infectious organism growth agent.

Clause 2. The transport media of Clause 1, comprising at least about 65% glycerol.

Clause 3. The transport media of Clause 1, comprising at least about 80% glycerol.

Clause 4. The transport media of Clause 1, comprising at least about 10% of a mucolytic agent.

Clause 5. The transport media of Clause 4, wherein the mucolytic agent comprises Sputolysin® (Dithiothrcitol).

Clause 6. The transport media of Clause 1, consisting essentially of glycerol and mucolytic agent.

Clause 7. The transport media of Clause 1, consisting of glycerol and mucolytic agent.

Clause 8. A method of transporting a biological sample, comprising: collecting the biological sample from a subject; and contacting the biological sample with a transport media, wherein the transport media comprises at least about 50% glycerol and at least about 5% of a mucolytic agent, wherein the transport media does not include any additional growth media, wherein the method improved yield and/or diagnosis of the biological sample.

Clause 9. The method of Clause 8, wherein contacting the sample with a transport media comprises placing the biological sample within a transport tube.

Clause 10 The method of Clause 9, wherein the transport tube comprises a screen.

Clause 11. The method of Clause 10, wherein the screen comprises a conical screen.

Clause 12. The method of Clause 11, further comprising moving the conical screen to a closed distal end of the transport tube.

Clause 13. The method of Clause 9, wherein the transport tube comprises an integrated sampling brush.

Clause 14. The method of Clause 8, further comprising transporting the biological sample to a sample diagnostic center.

Clause 15. The method of Clause 8, further comprising cooling the biological sample.

Clause 16. The method of Clause 15, further comprising shaking the biological sample prior to cooling.

Clause 17. The method of Clause 15, wherein cooling the biological sample comprises freezing the biological sample.

Clause 18. The method of Clause 8, further comprising agitating the sample to homogenize the specimen prior to culture.

Clause 19. The method of Clause 8, further comprising incubating the sample at 37 degrees Celsius for up to 24 hours to increase the density of pathogenic bacteria prior to culture.

Clause 20. An infectious organism transport system, comprising: a transport media as in any of Clause 1-7; and a transport tube.

Clause 21. The transport system of Clause 20, wherein the transport tube comprises a screen.

Clause 22. The transport system of Clause 21, wherein the screen comprises a conical screen.

Clause 23. The transport system of Clause 21, wherein the screen is axially movable.

Clause 24. The transport system of Clause 20, further comprising a storage case comprising a plurality of wells configured to fit a plurality of transport tubes.

Clause 25. The transport system of Clause 24, further comprising a cooling container, the cooling container comprising a cavity configured to house the storage case therein.

Clause 26. The transport system of Clause 25, further comprising a Pelican case configured to house the cooling container therein.

Clause 27. The transport system of Clause 20, wherein the transport tube comprises a generally conical distal end.

Clause 28. The transport system of Clause 20, wherein the transport tube comprises a generally flat distal end.

Clause 29. The transport system of Clause 20, wherein the transport tube comprises an open end that comprises a diameter greater than that of a diameter of a more distal tubular portion of the transport tube.

Clause 30. The transport system of Clause 20, wherein the transport tube comprises an open end that comprises a diameter equal to that of a diameter of a more distal tubular portion of the transport tube.

Clause 31. A modular biological sample container, comprising:
an upper section comprising a first lumen configured to be reversibly closed with a first cap;
a lower section comprising a second lumen configured to be reversibly closed with a second cap;
a funnel portion proximate a top end of the upper section;
a cylindrical portion proximate the funnel portion;
a transition zone between the funnel portion and the cylindrical portion; and reversible connectors configured such that the upper section can be reversibly attached and/or detached from the lower section.

Clause 32. The sample container of Clause 31, further comprising a screen within the lower section.

Clause 33. The sample container of Clause 31, wherein the first lumen comprises a diameter greater than a diameter of the second lumen.

Clause 34. The sample container of Clause 31, wherein the reversible connectors comprise threaded surfaces.

Clause 35. The sample container of Clause 34, wherein the threaded surfaces comprise an inner sidewall of the upper section and an outer sidewall of the lower section.

Clause 36. The sample container of Clause 31, comprising threaded surfaces proximate a top end of the upper section and a bottom end of the lower section.

Clause 37. The sample container of Clause 31, wherein the second cap is removably coupled to the bottom end of the lower section when the upper section is coupled to the lower section.

Clause 38. A modular biological sample kit, comprising: the sample container of Clause 31, and a third cap configured to reversibly close the transition zone following detachment of the funnel portion from the cylindrical portion.

Clause 39. A screen for a modular biological transport container, comprising:
a first open end comprising a first diameter,
a second open end comprising a second diameter,
a conical section comprising a sidewall defining a flow path between the first open end and the second open end,
wherein the conical section comprises pores, and
wherein the second diameter is smaller than the first diameter.

Clause 40. The screen of Clause 39, wherein an axial length of the conical section is between about 1 cm and about 5 cm.

Clause 41. The screen of Clause 39, wherein the conical section slopes radially inwardly at an angle of between about 33 degrees and about 75 degrees.

Clause 42. The screen of Clause 39, wherein the pores comprise a diameter of between about 0.5 mm and about 7 mm.

Clause 43. The screen of Clause 39, wherein the pores comprise a diameter of between about 3 mm and about 5 mm.

Clause 44. The screen of Clause 39, wherein the second diameter that is between about 25% and about 75% of the first diameter.

Clause 45. The screen of Clause 39, wherein the second diameter is greater than the diameter of each of the pores.

Clause 46. A method of collecting organisms on transport media, comprising:
contacting a biological sample with sample transport media, the transport media comprising at least about 50% glycerol, and at least about 5% of a mucolytic agent, wherein the infectious organism transport media does not include any additional infectious organism growth agent; and
sending the sample to a laboratory for culturing.

Clause 47. The method of Clause 46, wherein contacting the biological sample comprises placing the biological sample in a transport tube comprising the sample transport media, a screen, and a sampling brush.

Clause 48. A method of culturing organisms on transport media, comprising:
receiving a biological sample associated with transport media, the transport media comprising at least about 50% glycerol, and at least about 5% of a mucolytic agent, wherein the infectious organism transport media does not include any additional infectious organism growth agent; and incubating the biological sample to culture one or more organisms.

Clause 49. The method of Clause 48, further comprising identifying the one or more cultured organisms.

Clause 50. The method of Clause 48, wherein the cultured organisms comprise bacterial organisms.

Clause 51. The method of Clause 48, wherein the cultured organisms comprise viral organisms.

Clause 52. The method of Clause 48, wherein the cultured organisms comprise fungal organisms.

Clause 53. The method of Clause 48, wherein the cultured organisms comprise parasitic organisms.

Clause 54. The method of Clause 48, wherein the one or more cultured organisms is selected from the group consisting of: *Haemophilus influenzae, Klebsiella pneumoniae, Acinetobacter baumannii, Pseudomonas aeruginosa, Stenotrophomonas maltophilia, Streptococcus pneumonia, Moraxella catarrhalis, Serratia marcescans, Pasteurella multocida*, Group G *streptococcus, Citrobacter freundii, Enterobacter aerogenes, Proteus mirabilis*, extended-spectrum beta-lactamase producing *Enterobacteraciae*, methicillin-resistant *Staphylococcus aureus*, multi-drug resistant *Streptococcus pneumoniae, Helicobacter pylori, Mycobacterium tuberculosis, Mycobacterium avium-intracellulare*, other *mycobacterium*, and vancomycin-resistant *Enterococcus*.

Clause 55. The method of Clause 49, wherein the cultured organisms can be identified within about 36 hours after incubation or after sample collection.

Clause 56. The method of Clause 49, wherein the cultured organisms can be identified within about 24 hours after incubation or after sample collection.

Clause 57. The method of Clause 48, further comprising freezing and thawing the biological sample, wherein the biological sample is frozen and thawed while preserving cellular wall integrity.

Clause 58. The method of Clause 48, further comprising incubating the sample at a desired temperature for up to 24 hours in order to increase the density of bacteria in samples with low initial bacterial density at collection.

Clause 59. The method of Clause 58, wherein the desired temperature is about 37° C.

Clause 60 The method of Clause 49, further comprising performing antimicrobial sensitivity studies on the cultured organisms.

Clause 61. A biological transport system, comprising any number of features disclosed herein.

Clause 62. A method of culturing organisms on transport media, comprising any number of features as disclosed herein.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "placing a sample in a transport tube" includes "instructing the placing of a sample in a transport tube." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A method of storing an infectious organism, comprising: collecting an *H. pylori* sample from a subject; and contacting the *H. pylori* sample with a transport media, wherein the transport media comprises at least 50% glycerol and at least 5% of mucolytic agent, wherein the transport media does not include any growth media other than glycerol.

2. The method of claim 1, wherein the *H. pylori* sample can be identified within 24 hours after sample collection.

3. The method of claim 1, wherein the *H. pylori* sample is recovered from gastric contents using a string test.

4. The method of claim 1, further comprising incubating the *H. pylori* sample at 37 degrees Celsius for up to 24 hours to increase the density of *H. pylori* prior to culture after contacting the *H. pylori* sample with the transport media.

5. The method of claim 1, further comprising assessing antibiotic sensitivity of the *H. pylori* sample after contacting the *H. pylori* sample with the transport media.

6. The method of claim 1, further comprising freezing the *H. pylori* sample after contacting the *H. pylori* sample with the transport media.

7. The method of claim 1, wherein the remainder of the transport media that is not glycerol or mucolytic agent is a sterile fluid selected from sterile water or saline.

8. The method of claim 1, wherein the transport media comprises at least 5-15% of a mucolytic agent.

9. The method of claim 8, wherein the transport media comprises at least 60% of glycerol.

10. The method of claim 1, wherein the mucolytic agent comprises dithiothreitol (DTT).

11. A method of transporting an *H. pylori* sample, comprising: collecting the *H. pylori* sample from a subject; and contacting the *H. pylori* sample with a transport media, wherein the transport media comprises at least 60% glycerol and at least 5% of mucolytic agent, wherein the transport media does not include any growth media other than the glycerol.

12. The method of claim 11, wherein the *H. pylori* sample can be identified within 24 hours after sample collection.

13. The method of claim 11, further comprising assessing antibiotic sensitivity of the *H. pylori* sample after contacting the *H. pylori* sample with the transport media.

14. The method of claim 11, further comprising freezing the *H. pylori* sample after contacting the *H. pylori* sample with the transport media.

15. The method of claim 11, wherein the transport media comprises at least 5-15% of a mucolytic agent.

16. The method of claim 11, wherein the mucolytic agent comprises dithiothreitol (DTT).

17. A method of culturing an *H. pylori* sample on transport media, comprising: receiving the *H. pylori* sample associated with transport media, the transport media comprising at least 50% glycerol, and at least 5% of a mucolytic agent, wherein the infectious organism transport media does not include any additional infectious organism growth agent; and incubating the *H. pylori* sample to culture one or more organisms.

18. The method of claim 17, further comprising assessing antibiotic sensitivity of the *H. pylori* sample.

19. The method of claim 17, wherein the transport media comprises at least 5-15% of a mucolytic agent.

20. The method of claim 17, wherein the transport media comprises at least 60% glycerol.

* * * * *

UNITED STATES PATENT AND TRADEMARK OFFICE
CERTIFICATE OF CORRECTION

| | | |
|---|---|---|
| PATENT NO. | : 12,312,579 B2 | Page 1 of 2 |
| APPLICATION NO. | : 17/354218 | |
| DATED | : May 27, 2025 | |
| INVENTOR(S) | : Thomas A. Cumbo et al. | |

It is certified that error appears in the above-identified patent and that said Letters Patent is hereby corrected as shown below:

In the Specification

Column 1, Line 56, delete "(e.g., (. difficile" and insert -- (e.g., C. difficile --.

Column 5, Line 58, delete "baumannii, aeruginosa, Stenotrophomonas" and insert -- baumannii, Pseudomonas aeruginosa, Stenotrophomonas --.

Column 5, Line 59, delete "Serratia marcescans, Pasteurella" and insert -- Serratia marcescens, Pasteurella --.

Column 5, Line nos. 62-63, delete "producing Enterobacteraciae, methicillin" and insert -- producing Enterobacteriaceae, methicillin --.

Column 6, Line 38, delete "1L-10 illustrates" and insert -- 1L-1O illustrates --.

Column 8, Line 4, delete "cases), Dithiocrythritol (DTE);" and insert -- cases), Dithioerythritol (DTE); --.

Column 8, Line 5, delete "2-carboxyethyphosphine (TCEP)," and insert -- 2-carboxyethylphosphine (TCEP), --.

Column 9, Line 18, delete "broth, tiogycolate broth," and insert -- broth, thioglycolate broth, --.

Figure 10:
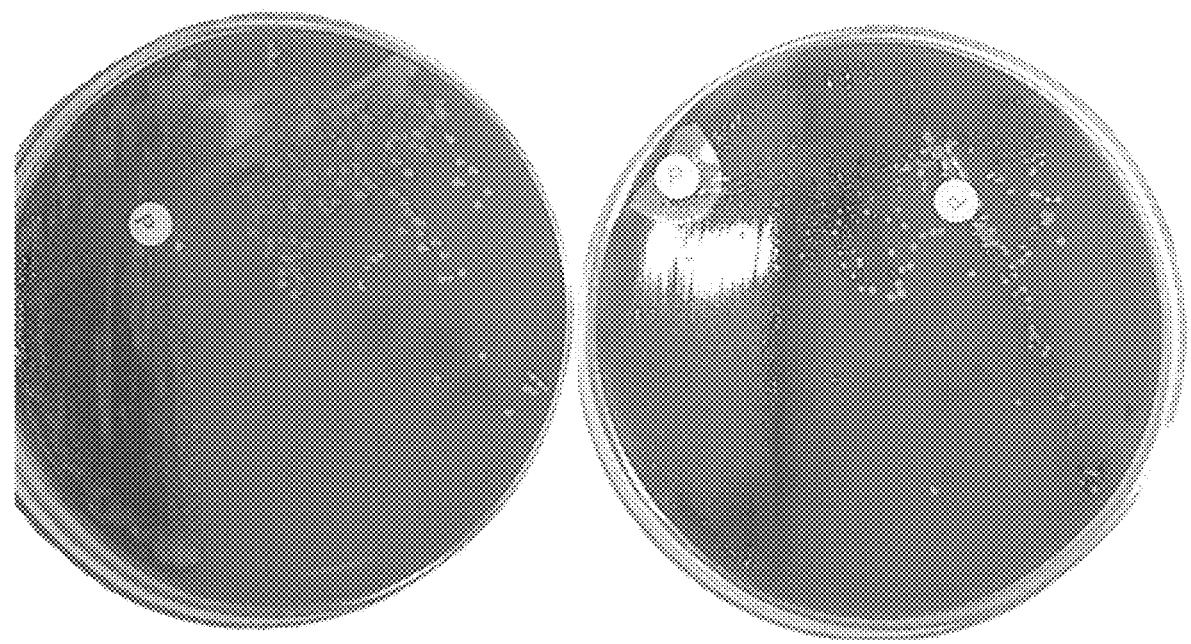

Column 14, Line 26, delete "FIG. 10 illustrates" and insert -- FIG. 1O illustrates --.

Column 14, Line 45, delete "Serratia marcescans, Pasteurella" and insert -- Serratia marcescens, Pasteurella --.

Column 14, Line nos. 47-48, delete "producing Enterobacteraciae, methicillin" and insert -- producing Enterobacteriaceae, methicillin --.

Signed and Sealed this
Twenty-second Day of July, 2025

Coke Morgan Stewart
*Acting Director of the United States Patent and Trademark Office*

CERTIFICATE OF CORRECTION (continued)
U.S. Pat. No. 12,312,579 B2

Column 17, Line 63, delete "5 mm,6 mm," and insert -- 5 mm, 6 mm, --.

Column 26, Line 43 (approx.), delete "FIG. 50 illustrates" and insert -- FIG. 5O illustrates --.

Column 30, Line 6, delete "Serratia marcescans, Pasteurella" and insert -- Serratia marcescens, Pasteurella --.

Column 30, Line 9-10, delete "producing Enterobacteraciae, methicillin" and insert -- Producing Enterobacteriaceae, methicillin --.

Column 30, Line 50, delete "Sputolysin® (Dithiothrcitol)." and insert -- Sputolysin® (Dithiothreitol). --.

Column 33, Line 18, delete "Serratia marcescans, Pasteurella" and insert -- Serratia marcescens, Pasteurella --.

Column 33, Line 21, delete "producing Enterobacteraciae, methicillin" and insert -- producing Enterobacteriaceae, methicillin --.